United States Patent [19]
Burkholder et al.

[11] Patent Number: 5,597,845
[45] Date of Patent: Jan. 28, 1997

[54] SUBSTITUTED ALKYLDIAMINE DERIVATIVES

[75] Inventors: Timothy P. Burkholder, Fairfield; Elizabeth M. Kudlacz; Tieu-Binh Le, both of Cincinnati, all of Ohio

[73] Assignee: Merrell Pharmaceuticals Inc., Cincinnati, Ohio

[21] Appl. No.: 262,209

[22] Filed: Jun. 20, 1994

[51] Int. Cl.$^6$ .................. C07D 209/18; C07D 407/06; A61K 31/405
[52] U.S. Cl. .................. 514/419; 548/494; 548/495
[58] Field of Search .................. 548/495, 494; 514/419

[56] References Cited

FOREIGN PATENT DOCUMENTS

| 0394989 | 10/1990 | European Pat. Off. . |
|---------|---------|----------------------|
| 9404494 | 3/1994  | WIPO . |

*Primary Examiner*—David B. Springer
*Attorney, Agent, or Firm*—David M. Stemerick

[57] ABSTRACT

The present invention relates to novel substituted alkyldiamine derivatives and pharmaceutically acceptable salts thereof which are useful tachykinin antagonists. Such antagonists are useful in the treatment of tachykinin-mediated diseases and conditions including asthma, cough, and bronchitis.

40 Claims, No Drawings

SUBSTITUTED ALKYLDIAMINE DERIVATIVES

The present invention relates to novel substituted alkyldiamine derivatives (herein referred to as a compound or compounds of formula (1)) and their use as tachykinin receptor antagonists. Such antagonists are useful in the treatment of tachykinin-mediated diseases and conditions disclosed herein including: asthma, cough, and bronchitis.

SUMMARY OF THE INVENTION

The present invention provides novel substituted alkyldiamine derivatives of the formula:

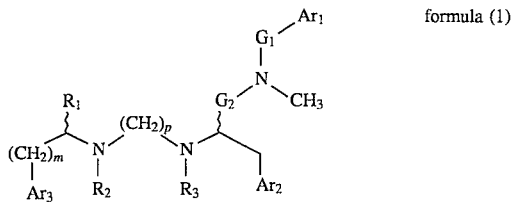

formula (1)

wherein $G_1$ is —$CH_2$— or —C(O)—;

$G_2$ is —$CH_2$— or —C(O)—;

p is 2 or 3;

m is 0 or 1;

$R_1$ is hydrogen, $C_1$–$C_4$ alkyl, —CHO, —C(O)O$R_4$, or —C(O)NH$R_4$, wherein $R_4$ is hydrogen, benzyl, or $C_1$–$C_4$ alkyl;

$R_2$ is hydrogen, or $C_1$–$C_4$ alkyl, $R_3$ is hydrogen or —C(O)O$R_5$ wherein $R_5$ is benzyl or $C_1$–$C_4$ alkyl;

$Ar_1$ is a radical chosen from the group:

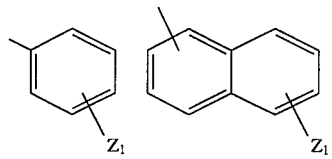

wherein $Z_1$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$Ar_2$ is a radical chosen from the group

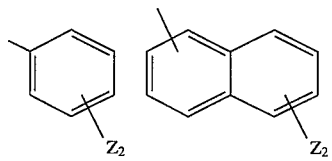

wherein $Z_2$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$Ar_3$ is a radical chosen from the group

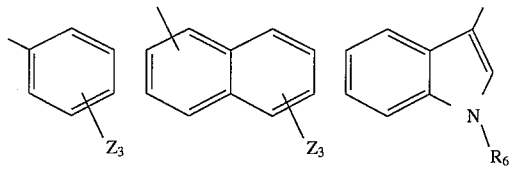

wherein $Z_3$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$R_6$ is hydrogen, $C_1$–$C_4$ alkyl, —CHO, —C(O)NH$R_7$, —($CH_2$)$_n$NHC(NH)NH$_2$, —($CH_2$)$_n$N(CH$_3$)$_2$, or —C(O)O$R_8$, wherein n is 2 or 3 and $R_7$ is hydrogen, benzyl, or $C_1$–$C_4$ alkyl and $R_8$ is benzyl or $C_1$–$C_4$ alkyl;

or stereoisomers, or pharmaceutically acceptable salt thereof.

As is appreciated by one of ordinary skill in the art the compounds of the formula (1) may exist as stereoisomers depending on the nature of the substituents present. Any reference in this application to one of the compounds of the formula (1) is meant to encompass either specific stereoisomers or a mixture of stereoisomers. Where indicated, the compounds follow the Cahn-Ingold-Prelog designation of (R)- and (S)- for the stereochemistry of compounds represented by formula (1).

The specific stereoisomers can be prepared by stereospecific synthesis using enatomerically pure or enatomerically enriched starting materials as are well known in the art. The specific stereoisomers can also be resolved and recovered by techniques known in the art, such as chromatography on chiral stationary phases, amide formation with a chiral acid followed by separation of the resultant diastereomeric amides and hydrolysis to the desired stereoisomer, or fractional recrystallization of addition salts formed by reagents used for that purpose, as described in "Enantiomers, Racemates, and Resolutions", J. Jacques, A. Collet, and S. H. Wilen, Wiley (1981). Specific stereoisomers, as required, can be prepared by stereoisomer resolution carried out on the precusors of starting materials, starting materials, intermediates, or the final products of formula (1).

As used in this application:

a) the term "halogen" refers to a fluorine atom, chlorine atom, bromine atom, or iodine atom;

b) the term "$C_1$–$C_4$ alkyl" refers to a branched or straight chained alkyl radical containing from 1 to 4 carbon atoms, such as methyl, ethyl, n-propyl, isopropyl, n-butyl, isobutyl, t-butyl, etc;

c) the term "$C_1$–$C_4$ alkoxy" refers to a straight or branched alkoxy group containing from 1 to 4 carbon atoms, such as methoxy, ethoxy, n-propoxy, isopropoxy, n-butoxy, isobutoxy, t-butoxy, etc;

d) the designation —C(O)— refers to a carbonyl group of the formula:

e) the designation "⌇" refers to a bond for which the stereochemistry is not designated;

f) the designations —$CO_2R$ and —C(O)OR refer to a group of the formula:

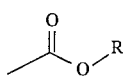

g) the designation —C(O)NHR refer to a group of the formula:

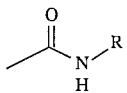

h) as used in the examples and preparations, the following terms have the meanings indicated: "g" refers to grams, "mg" refers to milligrams, "mmol" refers to millimoles, "mL" refers to milliliters, "°C." refers to degrees Celsius, "$R_f$" refers to retention factor, "mp" refers to melting point, "dec" refers to decomposition, "THF" refers to tetrahydrofuran, "DMF" refers to dimethylformamide, "M" refers to molar, "TLC" refers to thin layer chromatography, "HPLC" refers to high performance liquid chromatography, "HRMS" refers to high resolution mass spectrum;

i) by the designation

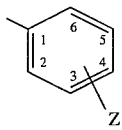

it is understood that the radical is attached at the 1-position and the substituent or substituents represented by Z can be attached in any of the 2, 3, 4, 5, or 6 positions;

j) by the designation

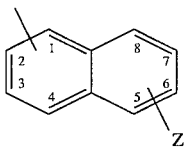

it is understood that the radical can be attached at the either the 1-position or the 2-position, it is further understood that when the radical is attached at the 1-position the substituent or substituents represented by Z can be attached in any of the 2, 3, 4, 5, 6, 7, or 8 positions and that when the radical is attached at the 2-position the substituent or substituents represented by Z can be attached in any of the 1, 3, 4, 5, 6, 7, or 8 positions;

k) the designation "p-1" used in regard to the aldehydes of structure (3) refers to an aldehyde of structure (3) which has one less methylene than is required for p in the final product and gives rise after a reductive amination to a compound in which p is as required in the final product of formula (1), therefore it is understood that aldehydes of structure (3) in which p-1 is 1 give rise to compounds of formula (1) in which p is 2 and that aldehydes of structure (3) in which p-1 is 2 give rise to compounds of formula (1) in which p is 3;

l) the term "pharmaceutically acceptable salts thereof refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Preferred embodiments of formula (1) are given below:

1) Compounds in which p is 2 are preferred;
2) Compounds in which $G_1$ is —$CH_2$— and $G_2$ is —C(O)— and $G_1$ is —C(O)— and $G_2$ —$CH_2$— are preferred, and compounds in which $G_1$ is —$CH_2$— and $G_2$ is —C(O)— are more preferred;
3) Compounds in which $R_2$ is hydrogen are preferred;
4) Compounds in which $R_3$ is hydrogen are preferred;
5) Compounds in which $R_1$ is hydrogen, $C_1$–$C_4$ alkyl, —C(O)O$R_4$, or —C(O)NH$R_4$ are preferred and compounds in which $R_1$ is —C(O)O$R_4$ or —C(O)NH$R_4$ are more preferred and compounds in which $R_1$ is —C(O)O$R_4$ are most preferred;
6) Compounds in which $Ar_3$ is the radical

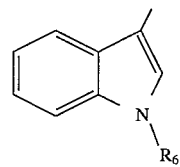

are preferred.

It is understood that further preferred embodiments of formula (1) can be selected by requiring one or more of the preferred embodiments 1 through 6 of formula (1) or by reference to examples given herein.

Examples of compounds encompassed by the present invention include the following. This list is meant to be representative only and is not intended to limit the scope of the invention in any way:

(S)-N-Benzyl-N-methyl-2-[[(S)-2-[(1H-indol-3-yl)-1-carboxymethyl]-ethylamino]-N'-(t-butoxycarbonyl)-ethylamino]-3-phenyl-propionamide;

(S)-N-Benzyl-N-methyl-2-[[(S)-2-[(1-methyl-indol-3-yl)-1-carboxymethyl]-ethylamino]-N'-(t-butoxycarbonyl)-ethylamino]-3-phenyl-propionamide;

(S)-N-Benzyl-N-methyl-2-[[(R)-2-[(1H-indol-3-yl)-1-carboxymethyl]-ethylamino]-N'-(t-butoxycarbonyl)-ethylamino]-3-phenyl-propionamide;

(S)-N-Benzyl-N-methyl-2-[[(S)-2-phenyl-1-carboxymethyl]-ethylamino]-N'-(t-butoxycarbonyl)-ethylamino-3-phenyl-propionamide;

(S)-N-Benzyl-N-methyl-2-[[(S)-1-phenyl-1-carboxymethyl-methylamino]-N'-(t-butoxycarbonyl)-ethylamino]-3-phenyl-propionamide;

(S)-N-Benzyl-N-methyl-2-[[2-(1H-indol-3-yl)-ethylamino]-N'-(t-butoxycarbonyl)-ethylamino]-3-phenyl-propionamide;

(S)-N-Benzyl-N-methyl-2-[[(R and S)-2-(1H-indol-3-yl)-1-methyl-ethylamino]-N'-(t-butoxycarbonyl)-ethylamino]-3-phenyl-propionamide;

(S)-N-Benzyl-N-methyl-2-[[(S)-2-(1H-indol-3-yl)-1-carboxylic acid amide-ethylamino]-N'-(t-butoxycarbonyl)ethylamino]-3-phenyl-propionamide;

(S)-N-(2-Methoxybenzyl)-N-methyl-2-[[(S)-2-(1H-indol-3-yl)-1-carboxymethyl-ethylamino]-N'-(t-butoxycarbonyl)-ethylamino]-3-phenyl-propionamide;

(S)-N-(3,4,5-Trimethoxybenzyl)-N-methyl-2-[[(S)-2-(1H-indol-3-yl)-1-carboxymethyl-N'-(t-butoxycarbonyl)ethylamino]ethylamino]-3-phenyl-propionamide;

(S)-N-Benzyl-N-methyl-2-[[(S)-2-(1H-indol-3-yl)-1-carboxymethyl-ethylamino]-N'-(t-butoxycarbonyl)ethylamino]-3-(naphth-2-yl)-propionamide;

(S)-N-(2-Methoxybenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide;

(S)-N-Benzyl-N-methyl-2-[[(S)-2-(1H-indol-3-yl)-1-carboxymethyl-ethylamino]-N'-(t-butoxycarbonyl)-propylamino]-3-phenyl-propionamide;

(S)-N-(3,4-Dichlorobenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide;

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-(3,4,5-trimethoxy)benzamide;

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-benzamide;

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-benzimide;

N-Methyl-N-benzyl-N-[(S)-2-[(S)-2-(1H-indol-3-yl)-1-carboxymethyl-ethylamino]-N'-(t-butoxycarbonyl)-ethylamino]-3-phenyl-propylamine;

(S)-N-Benzyl-N-methyl-2-[[(R)-2-(1H-indol-3-yl)-1-carboxymethyl-ethylamino]-ethylamino]-3-phenyl-propionamide;

(S)-N-Benzyl-N-methyl-2-[[(S)-2-(1H-indol-3-yl)-1-carboxymethyl-ethylamino]-ethylamino]-3-phenyl-propionamide;

(S)-N-Benzyl-N-methyl-2-[[(S)-2-[(1-methyl-indol-3-yl)-1-carboxymethyl]-ethylamino]-ethylamino]-3-phenyl-propionamide;

(S)-N-Benzyl-N-methyl-2-[[(S)-2-phenyl-1-carboxymethyl-ethylamino]-ethylamino]-3-phenyl-propionamide;

(S)-N-Benzyl-N-methyl-2-[[(S)-1-phenyl-1-carboxymethyl-ethyl-methylamino]-ethylamino]-3-phenyl-propionamide;

(S)-N-Benzyl-N-methyl-2-[[2-(1H-indol-3-yl)-ethylamino]]-ethylamino]-3-phenyl-propionamide;

(S)-N-Benzyl-N-methyl-2-[[(R and S)-2-(1H-indol-3-yl)-1-methyl-ethylamino]-ethylamino]-3-phenyl-propionamide;

(S)-N-Benzyl-N-methyl-2-[[(S)-2-(1H-indol-3-yl)-1-carboxylic acid amide-ethylamino]-ethylamino]-3-phenyl-propionamide;

(S)-N-(2-Methoxybenzyl)-N-methyl-2-[[(S)-2-(1H-indol-3-yl)-1-carboxymethyl-ethylamino]-ethylamino]-3-phenyl-propionamide;

(S)-N-(3,4,5-Trimethoxybenzyl)-N-methyl-2-[[(S)-2-(1H-indol-3-yl)-1-carboxymethyl-ethylamino]-ethylamino]-3-phenyl-propionamide;

(S)-N-Benzyl-N-methyl-2-[[(S)-2-(1H-indol-3-yl)-1-carboxymethyl-ethylamino]-ethylamino]-3-(naphth-2-yl)-propionamide;

(S)-N-(2-Methoxybenzy)-N-methyl-2-[[(S)-2-(1H-indol-3-yl)-1-carboxymethyl-ethylamino]-ethylamino]-3-(naphth-2-yl)-propionamide;

(S)-N-(3,4-Dichlorobenzyl)-N-methyl-2-[[(S)-2-(1H-indol-3-yl)-1-carboxymethyl-ethylamino]-ethylamino]-3-(naphth-2-yl)-propionamide;

N-Methyl-N-[(S)-2-[[(S)-2-(1H-indol-3-yl)-1-carboxymethyl-ethylamino]-ethylamino]-3-phenyl-propyl]-(3,4,5-trimethoxy)benzamide;

N-Methyl-N-[(S)-2-[[(S)-2-(1H-indol-3-yl)-1-carboxymethyl-ethylamino]-ethylamino]-3-phenyl-propyl]-benzamide;

(S)-N-Methyl-N-[(S)-2-[[(S)-2-(1H-indol-3-yl)-1-carboxymethyl-ethylamino]-ethylamino]-3-phenyl-propyl]-benzimide;

(S)-N-Methyl-N-benzyl-N-[(S)-2-[(S)-2-(1H-indol-3-yl)-1-carboxymethyl-ethylamino]-ethylamino]-3-phenyl-propylamine;

(S)-N-Benzyl-N-methyl-2-[[(S)-2-[(1-(3-dimethylamino-propyl)-indol-3-yl)-1-carboxymethyl]-ethylamino]-ethylamino]-3-phenyl-propionamide;

(S)-N-Benzyl-N-methyl-2-[[(S)-2-(1-carboxyethyl-indol-3-yl)-1-carboxymethyl-ethylamino]-ethylamino]-3-(naphth-2-yl)-propionamide;

(S)-N-Benzyl-N-methyl-2-[[(S)-2-(1H-indol-3-yl)-1-carboxy-ethylamino]-ethylamino]-3-phenyl-propionamide.

The compounds of formula (1) may be synthesized by use of the following synthetic procedures to produce intermediates or final compounds of the invention:

Scheme A relates to the synthesis of compounds of formula (1).

Scheme B relates to the synthesis of the aldehyde of structure (3) in which $G_1$ is —$CH_2$— and $G_2$ is —C(O)— used as a starting material in Scheme A.

Scheme C relates to the synthesis of the aldehyde of structure (3) in which $G_1$ is —C(O)— and $G_2$ is —$CH_2$— used as a starting material in Scheme A.

Scheme D relates to the synthesis of the aldehyde of structure (3) in which $G_1$ is —C(O)— and $G_2$ is —C(O)— used as a starting material in Scheme A.

Scheme E relates to the synthesis of the aldehyde of structure (3) in which $G_1$ is —$CH_2$— and $G_2$ is —$CH_2$— used as a starting material in Scheme A.

A general synthetic procedure for preparing these compounds of formula (1) is set forth in Scheme A. The reagents and starting materials are readily available to one of ordinary skill in the art. In Scheme A, all substituents, unless otherwise indicated, are as previously defined.

SCHEME A

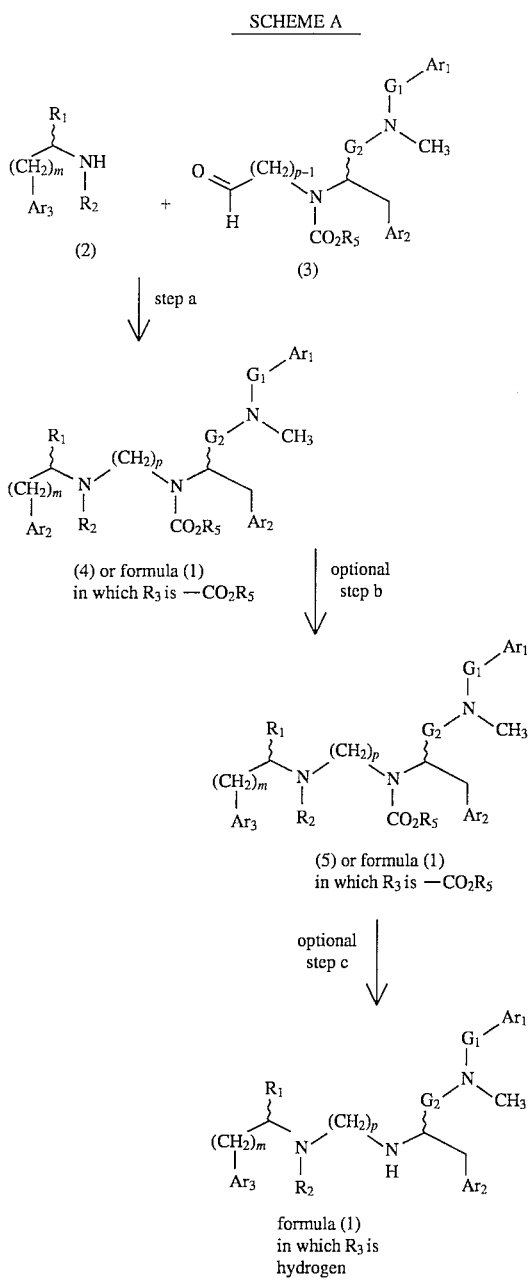

In Scheme A, step a, an appropriate amine of structure (2) or a salt of an appropriate amine of structure (2) is contacted with an appropriate aldehyde of structure (3) in a reductive amination to give a compound of structure (4). Compounds of structure (4) are compounds of formula (1) in which $R_3$ is —C(O)O$R_5$.

An appropriate amine of structure (2) is one in which the stereochemistry, $Ar_3$, $R_1$, $R_2$, and m are as desired in the final product of formula (1). An appropriate amine of structure (2) can also be one in which the stereochemistry is as desired in the final product of formula (1) and any of $Ar_3$, $R_1$, and $R_2$ give rise after deprotection or modification to $Ar_3$, $R_1$, and $R_2$ as desired in the final product of formula (1). An appropriate amine of structure (2) can also be one in which the stereochemistry gives rise after resolution to stereochemistry as desire in the final product of formula (1) and $Ar_3$, $R_1$, $R_2$, and m are as desired in the final product of formula (1). An appropriate amine of structure (2) can also be one in which the stereochemistry gives rise after resolution to stereochemistry as desire in the final product of formula (1) and any of $Ar_3$, $R_1$, and $R_2$ give rise after deprotection or modification to $Ar_3$, $R_1$, and $R_2$ as desired in the final product of formula (1).

Amines of structure (2) are readily prepared by methods known in the art. Some of the amines of structure (2) are prepared from α-amino-acids which can be obtained by methods known in the art or analogously known in the art, such as D. A. Evans, et al. *JACS* 112, 4011–4030 (1990); S. Ikegami et al. *Tetrahedron* 44, 5333–5342 (1988); W. Oppolzer et al. *Tet. Lets.* 30, 6009–6010 (1989); "Synthesis of Optically Active α-Amino-Acids", R. M. Williams (Pergamon Press, Oxford 1989); M. J. O'Donnell ed.: α-Amino-Acid Synthesis", *Tetrahedron Symposia in print, No. 33, Tetrahedron* 44, No. 17 (1988); U. Schöllkopf, *Pure Appl. Chem.* 55, 1799 (1983); U. Hengartner et al. *JOC* 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *JACS* 110, 8520–8525 (1988).

An appropriate aldehyde of structure (3) is one in which the stereochemistry, $G_1$, $G_2$, $R_5$, $Ar_1$, $Ar_2$, and p are as is desired in the final product of formula (1). An appropriate aldehyde of structure (3) can also be one in which the stereochemistry is as desired in the final product of formula (1) and any of $Ar_1$ and $Ar_2$, and $R_5$ give rise after deprotection $Ar_1$ and $Ar_2$ and $R_3$ are as desired in the final product of formula (1). An appropriate aldehyde of structure (3) can also be one in which the stereochemistry gives rise after resolution to stereochemistry as desire in the final product of formula (1) and $Ar_1$ and $Ar_2$ and $R_3$ are as desired in the final product of formula (1). An appropriate aldehyde of structure (3) can also be one in which the stereochemistry gives rise after resolution to stereochemistry as desire in the final product of formula (1) and any of $Ar_1$ and $Ar_2$, and $R_5$ give rise after deprotection $Ar_1$ and $Ar_2$ and $R_3$ are as desired in the final product of formula (1). For the preparation of compounds of formula (1) in which $R_3$ is hydrogen the use of aldehydes (3) in which $R_5$ is t-butyl is preferred.

For example, an appropriate amine of structure (2) or a salt of an appropriate amine of structure (2) is contacted with an appropriate aldehyde of structure (3). The reaction is carried out using a molar excess of a suitable reducing agent such as sodium borohydride or sodium cyanoborohydride with sodium cyanoborohydride being preferred. The reaction is carried out in a suitable solvent, such as methanol. Generally, the reaction is carried out at temperatures of from 0° C. to 50° C. Generally, the reactions require 1 to 72 hours. The product can be isolated and purified by techniques well known in the art, such as extraction, evaporation, chromatography, and recrystallization.

In Scheme A, optional step b, the groups $Ar_1$, $Ar_2$, $Ar_3$ $R_1$, and $R_2$ of the compound of structure (5) may be deprotected or modified to give $Ar_1$, $Ar_2$, $Ar_3$, $R_1$, and $R_2$ as desired in the final product of formula (1). Compounds of structure (5) are compounds of formula (1) in which $R_3$ is —C(O)O$R_5$.

A deprotection reaction encompasses the hydrolysis of esters, the removal of a hydroxy protecting group, and the removal of an amine protecting group. The selection, use, and removal of protecting groups utilizing suitable protecting groups such as those described in *Protecting Groups in Organic Synthesis* by T. Greene, Wiley-Interscience (1981) is well known and appreciated in the art.

A modification reaction encompasses the formation of amides, the alkylation of an amine, the reduction of an ester and subsequent oxidation of the alcohol obtained to an aldehyde, an addition reaction to an indole nitrogen, or the formation of an amidate. Modification reactions are well known and appreciated in the art, such as those described in International Patent Application No. WO 93/14113 published Jan. 10, 1993; L. H. Werner et al *JACS* 79, 1675 (1957); L. H. Zhang and J. M. Cook *Heterocycles* 27, 2795 (1988). A modification reaction may require the use of a protecting group in compounds of structure (5) in which $R_2$ is hydrogen. When such a protecting group is required the t-BOC or the carbonylbenzyloxy (CBZ) protecting group can be used. The introduction of the t-BOC protecting group or the carbonylbenzyloxy (CBZ) is well known and appreciated in the art and is described in *Protecting Groups in Organic Synthesis* by T. Greene, Wiley-Interscience (1981).

In Scheme A, optional step c, the —$CO_2R_5$ group of an appropriate compound of structure (5) in which $R_5$ is t-butyl is removed by reaction with protic acid to give a compound of formula (1) in which $R_3$ is hydrogen or a salt of a compound of formula (1) in which $R_3$ is hydrogen.

For example, an appropriate compound of structure (5) is reacted with a protic acid. The reaction is carried out in a solvent, such as ethyl acetate, dioxane, methanol, or ethanol. Generally, the reaction requires from 1 to 48 hours and is carried out at ambient temperature. The product can be isolated and purified by techniques well known in the art, such as extraction, evaporation, chromatography, and recrystallization.

As is appreciated to one skilled in the art, in Scheme A the number and order in which optional step b and optional step c are carried out will depend on the compound Of formula (1) which is desired as the product of Scheme A. For example, some compounds of formula (1), may be prepared by sequential modification and deprotection, such as alkylation of an amine, optional step b, removal of the amino protecting group, optional step c, followed by an ester hydrolysis, optional step b.

The following examples present typical syntheses as described in Scheme A. These examples are understood to be illustrative only and are not intended to limit the scope of the invention in any way.

EXAMPLE 1

(S)-N-Benzyl-N-methyl-2-[[(S)-2-[(1H-indol-3-yl)-1-carboxymethyl]-ethylamino]-N'-(t-butoxycarbonyl)-ethylamino]-3-phenyl-propionamide Scheme A, step a:
Combine (S)-N-benzyl-N-methyl-2-[N'-(t-butoxycarbonyl)-2-oxo-ethylamino]-3-phenyl-propionamide (4.87 g, 11.87 mmol) and (S)-2-(1H-indol-3-yl)-1-carboxymethyl-ethylamine hydrochloride salt ((S)-tryptophan methyl ester hydrochloride salt) (3.02 g, 11.86 mmol) in methanol (120 mL). Add dropwise, a solution of sodium cyanoborohydride (9.5 mL, 1M in THF, 9.5 mmol) and stir under an inert atmosphere for 48 hours. Concentrate in vacuo to obtain a residue. Dilute the residue with ethyl acetate and extract with water. Separate the layers, dry the organic layer over $MgSO_4$, filter, and evaporate in vacuo to give a residue. Chromatograph the residue on silica gel eluting with 3% methanol/dichloromethane to give the title compound: TLC $R_f$=0.57 (silica gel, 10% methanol/dichloromethane).

EXAMPLE 2

(S)-N-Benzyl-N-methyl-2-[[(S)-2-[(1-methyl-indol-3-yl)-1-carboxymethyl]-ethylamino]-N'-(t-butoxycarbonyl)-ethylamino]-3-phenyl-propionamide Scheme A, step a:
Prepare by the method of Example 1 using (S)-2-(1-methyl-indol-3-yl)-1-carboxymethyl-ethylamine hydrochloride salt (Lin-Hua Zhang and James M. Cook *Heterocycles* 27, 2795–2802 (1988)) (1.0 mmol) and (S)-N-benzyl-N-methyl-2-[N'-(t-butoxycarbonyl)-2-oxo-ethylamino]-3-phenyl-propionamide (1.0 mmol) to give the title compound.

EXAMPLE 3

(S)-N-Benzyl-N-methyl-2-[[(R)-2-[(1H-indol-3-yl)-1-carboxymethyl]-ethylamino]-N'-(t-butoxycarbonyl)-ethylamino]-3-phenyl-propionamide Scheme A, step a:
Prepare by the method of Example 1 using (R)-2-(1H-indol-3-yl)-1-carboxymethyl-ethylamine hydrochloride salt ((R)-tryptophan methyl ester hydrochloride salt) (0.25 g, 1.0 mmol) and (S)-N-benzyl-N-methyl-2-[N'-(t-butoxycarbonyl)-2-oxo-ethylamino]-3-phenyl-propionamide (0.41 g, 1.0 mmol) to give the title compound: TLC $R_f$=0.54 (silica gel, 10% methanol/dichloromethane).

EXAMPLE 4

(S)-N-Benzyl-N-methyl-2-[[(S)-2-phenyl-1-carboxymethyl]-ethylamino]-N'-(t-butoxycarbonyl)-ethylamino-3-phenyl-propionamide Scheme A, step a:
Prepare by the method of Example 1 using (S)-2-amino-3-phenyl-propionic acid methyl ester hydrochloride salt ((S)-phenylalanine methyl ester hydrochloride salt) (0.26 g, 1.0 mmol) and (S)-N-benzyl-N-methyl-2-[N'-(t-butoxycarbonyl)-2-oxo-ethylamino]-3-phenyl-propionamide (0.41 g, 1.0 mmol) to give the title compound: TLC $R_f$=0.51 (silica gel, 10% methanol/dichloromethane).

EXAMPLE 5

(S)-N-Benzyl-N-methyl-2-[[4(S)-1-phenyl-1-carboxymethyl-methylamino]-N'-(t-butoxycarbonyl)-ethylamino]-3-phenyl-propionamide Scheme A, step a:
Prepare by the method of Example 1 using (S)-1-amino-1-phenyl-acetic acid methyl ester hydrochloride salt ((S)-phenylglycine methyl ester hydrochloride salt) (1.0 g, 4.96 mmol) and (S)-N-benzyl-N-methyl-2-[N'-(t-butoxycarbonyl)-2-oxo-ethylamino]-3-phenyl-propionamide (2.04 g, 4.96 mmol) to give the title compound: TLC $R_f$=0.80 (silica gel, 10% methanol/dichloromethane).

EXAMPLE 6

(S)-N-Benzyl-N-methyl-2-[[2-(1H-indol-3-yl)-ethylamino]-N'-(t-butoxycarbonyl)-ethylamino]-3-phenyl-propionamide Scheme A, step a:

Prepare by the method of Example 1 using 2-(1H-indol-3-yl)-ethylamine hydrochloride salt (tryptamine hydrochloride salt) (0.197 g, 1.0 mmol) and (S)-N-benzyl-N-methyl-2-[N-(t-butoxycarbonyl)-2-oxo-ethylamino]-3-phenyl-propionamide (0.41 g, 1.0 mmol) to give the title compound: TLC $R_f$=0.69 (silica gel, 85% chloroform/10% methanol/5% acetic acid).

EXAMPLE 7

(S)-N-Benzyl-N-methyl-2-[[(R and S)-2-(1H-indol-3-yl)-1-methyl-ethylamino]-N'-(t-butoxycarbonyl)-ethylamino]-3-phenyl-propionamide Scheme A, step a:

Prepare by the method of Example 1 using (R and S)-2-(1H-indol-3-yl)-1-methyl-ethylamine hydrochloride salt ((R and S)-α-methyltryptamine hydrochloride salt) (0.174 g, 1.0 mmol) and (S)-N-benzyl-N-methyl-2-[N-(t-butoxycarbonyl)-2-oxo-ethylamino]-3-phenyl-propionamide (0.41 g, 1.0 mmol) to give the title compound: TLC $R_f$=0.35 (silica gel, 10% methanol/dichloromethane).

EXAMPLE 8

(S)-N-Benzyl-N-methyl-2-[[(S)-2-(1H-indol-3-yl)-1-carboxylic acid amide-ethylamino]-N'-(t-butoxycarbonyl)ethylamino]-3-phenyl-propionamide Scheme A, step a:

Prepare by the method of Example 1 using (S)-2-(1H-indol-3-yl)-1-(carboxylic acid amide)-ethylamine hydrochloride salt ((S)-tryptophanamide hydrochloride salt) (0.24 g, 1.0 mmol) and (S)-N-benzyl-N-methyl-2-[N'-(t-butoxycarbonyl)-2-oxo-ethylamino]-3-phenyl-propionamide (0.41 g, 1.0 mmol). Purify by chromatography eluting with 3% methanol/dichloromethane to give the title compound: TLC $R_f$=0.62 (silica gel, 10% methanol/dichloromethane).

EXAMPLE 9

(S)-N-(2-Methoxybenzyl)-N-methyl-2-[[(S)-2-(1H-indol-3-yl)-1-carboxymethyl-ethylamino]-N'-(t-butoxycarbonyl)-ethylamino]-3-phenyl-propionamide Scheme A, step a:

Prepare by the method of Example 1 using (S)-N-(2-methoxybenzyl)-N-methyl-2-[N'-(t-butoxycarbonyl)-2-oxo-ethylamino]-3-phenyl-propionamide (0.71 g, 1.6 mmol) and (S)-2-(1H-indol-3-yl)-1-carboxymethyl-ethylamine hydrochloride salt ((S)-tryptophan methyl ester hydrochloride salt) (0.45 g, 1.76 mmol). Purify by chromatography eluting with 50% ethyl acetate/hexane to give the title compound: TLC $R_f$=0.56 (silica gel, 50% ethyl acetate/hexane)

EXAMPLE 10

(S)-N-(3,4,5-Trimethoxybenzyl)-N-methyl-2-[[(S)-2-(1H-indol-3-yl)-1-carboxymethyl-ethylamino]N'-(t-butoxycarbonyl)-ethylamino]-3-phenyl-propionamide Scheme A, step a:

Prepare by the method of Example 1 using (S)-N-(3,4,5-trimethoxybenzyl)-N-methyl-2-[N'-(t-butoxycarbonyl)-2-oxo-ethylamino]-3-phenyl-propionamide (0.25 g, 1.0 mmol) and (S)-2-(1H-indol-3-yl)-1-carboxymethyl-ethylamine hydrochloride salt ((S)-tryptophan methyl ester hydrochloride salt) (0.41 g, 1.0 mmol). Purify by chromatography eluting sequentially with 1% methanol/dichloromethane and 5% methanol/dichloromethane to give the title compound: TLC $R_f$=0.83 (silica gel, 10% methanol/dichloromethane).

EXAMPLE 11

(S)-N-Benzyl-N-methyl-2-[[(S)-2-(1H-indol-3-yl)-1-carboxymethyl-ethylamino]-N'-(t-butoxycarbonyl)ethylamino]-3-(naphth-2-yl)-propionamide Scheme A, step a:

Prepare by the method of Example 1 using (S)-N-benzyl-N-methyl-2-[N'-(t-butoxycarbonyl)-2-oxo-ethylamino]-3-(2-napthyl)-propionamide (0.46 g, 1.0 mmol) and (S)-2-(1H-indol-3-yl)-1-carboxymethyl-ethylamine hydrochloride salt ((S)-tryptophan methyl ester hydrochloride salt) (0.26 g, 1.0 mmol). Purify by chromatography eluting with 5% methanol/dichloromethane to give the title compound: TLC $R_f$=0.34 (silica gel, 50% ethyl acetate/hexane).

EXAMPLE 12

(S)-N-(2-Methoxybenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide Scheme A, step a:

Prepare by the method of Example 1 using (S)-N-(2-methoxybenzyl)-N-methyl-2-[N'-(t-butoxycarbonyl)-2-oxo-ethylamino]-3-(naphth-2-yl)-propionamide (0.47 g, 0.96 mmol) and (S)-2-(1H-indol-3-yl)-1-carboxymethyl-ethylamine hydrochloride salt ((S)-tryptophan methyl ester hydrochloride salt) (0.28 g, 1.1 mmol). Purify by chromatography to give the title compound.

EXAMPLE 13

(S)-N-Benzyl-N-methyl-2-[[(S)-2-(1H-indol-3-yl)-1-carboxymethyl-ethylamino]-N'-(t-butoxycarbonyl)-propylamino]-3-phenyl-propionamide Scheme A, step a:

Prepare by the method of Example 1 using (S)-N-benzyl-N-methyl-2-[N'-(t-butoxycarbonyl)-3-oxo-propylamino]-3-phenyl-propionamide (2 mmol) and (S)-2-(1H-indol-3-yl)-1-carboxymethyl-ethylamine hydrochloride salt ((S)-tryptophan methyl ester hydrochloride salt) (2 mmol). Purify by chromatography to give the title compound.

EXAMPLE 14

(S)-N-(3,4-Dichlorobenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide Scheme A, Step a:

Prepare by the method of Example 1 using (S)-N-(3,4-dichlorobenzyl)-N-methyl-2-[N'-(t-butoxycarbonyl)-2-oxo-ethylamino]-3-(naphth-2-yl)-propionamide (0.29 g, 0.55 mmol) and (S)-2-(1H-indol-3-yl)-1-carboxymethyl-ethylamine hydrochloride salt ((S)-tryptophan methyl ester hydrochloride salt) (0.14 g, 0.55 mmol). Purify by chromatography eluting with 5% methanol/dichloromethane to give the title compound: TLC R$_f$=0.58 (silica gel, 50% ethyl acetate/hexane).

EXAMPLE 15

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-(3,4,5-trimethoxy)benzamide Scheme A step a:

Prepare by the method of Example 1 using (S)-N-methyl-N-[2-[N'-(t-butoxycarbonyl)-2-oxo-ethylamino]-3-phenyl-propyl]-(3,4,5-trimethoxy)benzamide (0.55 mmol) and (S)-2-(1H-indol-3-yl)-1-carboxymethyl-ethylamine hydrochloride salt ((S)-tryptophan methyl ester hydrochloride salt) (0.55 mmol). Purify by chromatography to give the title compound.

EXAMPLE 16

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-benzamide Scheme A step a:

Prepare by the method of Example 1 using (S)-N-methyl-N-[[2-[N'-(t-butoxycarbonyl)-2-oxo-ethylamino]-3-phenyl-propyl]-benzamide (0.11 g, 0.27 mmol) and (S)-2-(1H-indol-3-yl)-1-carboxymethyl-ethylamine hydrochloride salt ((S)-tryptophan methyl ester hydrochloride salt) (0.076 g, 0.3 mmol). Purify by chromatography eluting with 30% ethyl acetate/hexane to give the title compound.

EXAMPLE 17

N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-benzimide Scheme A step a:

Prepare by the method of Example 1 using (S)-N-Methyl-N-[[2-[N'-(t-butoxycarbonyl)-2-oxo-ethylamino]-3-phenyl-propyl]-benzimide (0.27 mmol) and (S)-2-(1H-indol-3-yl)-1-(carboxymethyl-ethylamine hydrochloride salt ((S)-tryptophan methyl ester hydrochloride salt) (0.3 mmol). Purify by chromatography to give the title compound.

EXAMPLE 18

N-Methyl-N-benzyl-N-[(S)-2-[(S)-2-(1H-indol-3-yl)-1-carboxymethyl-ethylamino]-N'-(t-butoxycarbonyl)-ethylamino]-3-phenyl-propylamine Scheme A, step a:

Prepare by the method of Example 1 using (S)-N-methyl-N-benzyl-N-[2-[N'-(t-butoxycarbonyl)-2-oxo-ethylamino]-3-phenyl-propylamine (0.5 mmol) and (S)-2-(1H-indol-3-yl)-1-(carboxymethyl-ethylamine hydrochloride salt ((S)-tryptophan methyl ester hydrochloride salt) (0.55 mmol). Purify by chromatography to give the title compound.

EXAMPLE 19

(S)-N-Benzyl-N-methyl-2-[[(S)-2-[(1H-indol-3-yl)-1-carboxymethyl]-N'''-(t-butoxycarbonyl)-ethylamino]-N'-(t-butoxycarbonyl)-ethylamino]-3-phenyl-propionamide Protection step:

Combine (S)-N-Benzyl-N-methyl-2-[[(S)-2-[(1H-indol-3-yl)-1-carboxymethyl]-ethylamino]-N'-(t-butoxycarbonyl)-ethylamino]-3-phenyl-propionamide (10 mmol) and di-t-butyl dicarbonate (10 mmol) in dichloromethane (50 mL). After 24 hours, evaporate in vacuo and chromatograph on silica gel to give the title compound.

EXAMPLE 20

(S)-N-Benzyl-N-methyl-2-[[(S)-2-(1H-indol-3-yl)-1-carboxymethyl-N'''-(t-butoxycarbonyl)-ethylamino]-N'-(t-butoxycarbonyl)ethylamino]-3-(naphth-2-yl)-propionamide Protection step:

Prepare by the method of Example 19 using (S)-N-Benzyl-N-methyl-2-[[(S)-2-(1H-indol-3-yl)-1-carboxymethyl-ethylamino]-N'-(t-butoxycarbonyl)ethylamino]-3-(naphth-2-yl)-propionamide.

EXAMPLE 21

(S)-N-Benzyl-N-methyl-2-[[(S)-2-[(1-(3-dimethylamino-propyl)-indol-3-yl)-1-carboxymethyl]-N'''-(t-butoxycarbonyl)-ethylamino]-N'-(t-butoxycarbonyl)-ethylamino]-3-phenyl-propionamide Scheme A, optional step b:

Combine (S)-N-Benzyl-N-methyl-2-[[(S)-2-[(1H-indol-3-yl)-1-carboxymethyl]-N'''-(t-butoxycarbonyl)-ethylamino]-N'-(t-butoxycarbonyl)-ethylamino]-3-phenyl-propionamide (5 mmol) and sodium amide (5 mmol, 50% suspension in toluene) in toluene (25 mL). Add 3-dimethylamino-1-chloropropane (5 mmol). After 24 hours, partition the reaction mixture between ethyl acetate and water. Separate the organic layer, dry over MgSO$_4$, filter and evaporate in vacuo to give a residue. Chromatograph the residue on silica gel to give the title compound.

EXAMPLE 22

(S)-N-Benzyl-N-methyl-2-[[(S)-2-(1-carboxyethyl-indol-3-yl)-1-carboxymethyl-N'''-(t-butoxycarbonyl)-ethylamino]-N'-(t-butoxycarbonyl)ethylamino]-3-(naphth-2-yl)-propionamide Scheme A, optional step b:

Prepare by the method of Example 20 using (S)-N-Benzyl-N-methyl-2-[[(S)-2-(1H-indol-3-yl)-1-carboxymethyl-N'''-(t-butoxycarbonyl)-ethylamino]-N'-(t-butoxycarbonyl)ethylamino]-3-(naphth-2-yl)-propionamide and ethyl chloroformate and purify by chromatography.

EXAMPLE 23

(S)-N-Benzyl-N-methyl-2-[[(R)-2-(1H-indol-3-yl)-
1-carboxymethyl-ethylamino]-ethylamino]-
3-phenyl-propionamide Scheme A, optional step c:

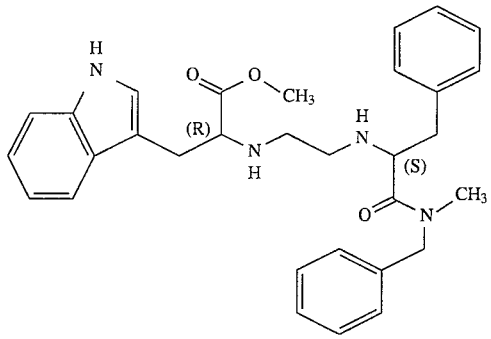

Combine (S)-N-benzyl-N-methyl-2-[[(R)-2-(1H-indol-3-yl)-1-carboxymethyl-ethylamino]-N'-(t-butoxycarbonyl)-ethylamino]-3-phenyl-propionamide (0.31 g, 0.5 mmol) and 4M hydrochloric acid in dioxane (10 mL) and stir for 1 hour. Evaporate in vacuo. Chromatograph eluting sequentially with 5% methanol/dichloromethane and 10% methanol/dichloromethane to give the title compound: TLC $R_f$=0.50 (silica gel, 10% methanol/dichloromethane). HRMS calculated for $C_{31}H_{37}N_4O_3$ 513.2865. Found 513.2839.

EXAMPLE 24

(S)-N-Benzyl-N-methyl-2-[[(S)-2-(1H-indol-3-yl)-
1-carboxymethyl-ethylamino]-ethylamino
3-3-phenyl-propionamide Scheme A, optional step c:

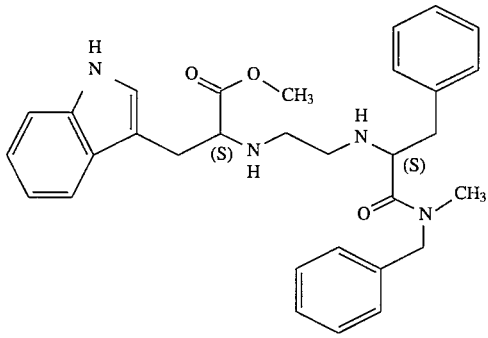

Prepare by the method of Example 23 using (S)-N-benzyl-N-methyl-2-[[(S)-2-(1H-indol-3-yl)-1-carboxymethyl-ethylamino]-N'-(t-butoxycarbonyl)-ethylamino]-3-phenyl-propionamide (1.15 g, 1.88 mmol) to give the title compound: TLC $R_f$=0.54 (silica gel, 10% methanol/dichloromethane); mp; 85°–86° C. HRMS calculated for $C_{31}H_{36}N_4O_3$ 512.2787. Found 512.2784.

EXAMPLE 25

(S)-N-Benzyl-N-methyl-2-[[(S)-2-[(1-methyl-indol-
3-yl)-1-carboxymethyl]-ethylamino]-ethylamino]-
3-phenyl-propionamide Scheme A, optional step c:

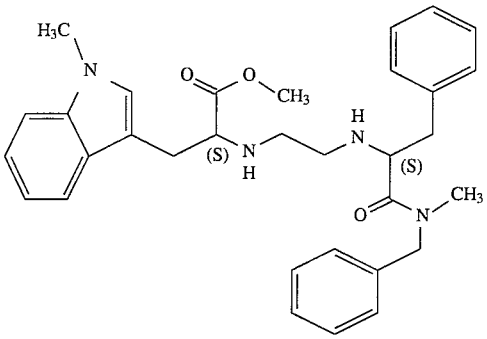

Prepare by the method of Example 23 using (S)-N-Benzyl-N-methyl-2-[[(S)-2-[(1-methyl-indol-3-yl)-1-carboxymethyl]-ethylamino]-N'-(t-butoxycarbonyl)-ethylamino]-3-phenyl-propionamide (0.88 mmol) to give the title compound.

EXAMPLE 26

(S)-N-Benzyl-N-methyl-2-[[(S)-2.-phenyl-
1-carboxymethyl-ethylamino]-ethylamino]-
3-phenyl-propionamide trifluoroacetic acid disalt Scheme A, optional step c:

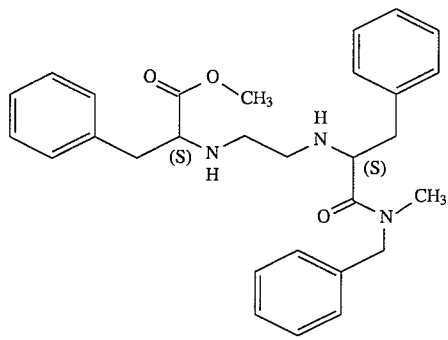

Prepare by the method of Example 23 using (S)-N-benzyl-N-methyl-2-[[(S)-2-phenyl-1-carboxymethyl-ethylamino]-N'-(t-butoxycarbonyl)-ethylamino]-3-phenyl-propionamide (0.28 g, 0.58 mmol) purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound: TLC $R_f$=0.51 (silica gel, 10% methanol/dichloromethane). HRMS calculated for $C_{29}H_{36}N_3O_3$ 474.2757. Found 474.2755.

EXAMPLE 27

(S)-N-Benzyl-N-methyl-2-[[(S)-1-phenyl-1-carboxymethyl-methylamino]-ethylamino]-3-phenyl-propionamide Scheme A, optional step c:

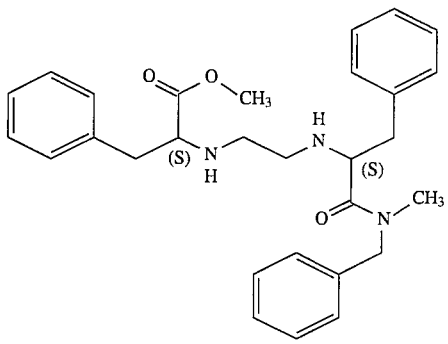

Prepare by the method of Example 23 using (S)-N-benzyl-N-methyl-2-[[(S)-1-phenyl-1-carboxymethyl-methylamino]-N'-(t-butoxycarbonyl)-ethylamino]-3-phenyl-propionamide (0.2 g, 0.36 mmol) and purify by chromatography eluting with 5% methanol/dichloromethane to give the title compound as a colorless oil: TLC $R_f$=0.76 (silica gel, 10% methanol/dichloromethane). Elem. Anal. calculated for $C_{28}H_{33}N_3O_3.0.25H_2O$: C, 72.47; H, 7.23, N, 9.05. Found: C, 72.47; H, 7.53, N, 9.10.

EXAMPLE 28

(S)-N-Benzyl-N-methyl-2-[[2-(1H-indol-3-yl)-ethylamino]]-ethylamino]-3-phenyl-propionamide trifluoroacetic acid disalt Scheme A, optional step c:

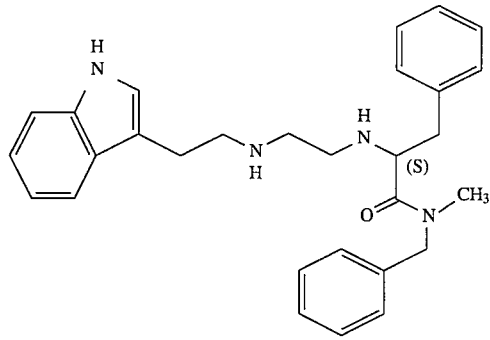

Prepare by the method of Example 23 using (S)-N-benzyl-N-methyl-2-[[2-(1H-indol-3-yl)-ethylamino]]-N'-(t-butoxycarbonyl)-ethylamino]-3-phenyl-propionamide (0.13 g, 0.24 mmol) and purify by chromatography eluting with 5% methanol/dichloromethane and further purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound: TLC $R_f$=0.37 (silica gel, 10% methanol/dichloromethane). HRMS calculated for $C_{29}H_{35}N_4O$ 455.2811. Found 455.2834.

EXAMPLE 29

(S)-N-Benzyl-N-methyl-2-[[(R and S)-2-(1H-indol-3-yl)-1-methyl-ethylamino]-ethylamino]-3-phenyl-propionamide trifluoroacetic acid disalt Scheme A, optional step c:

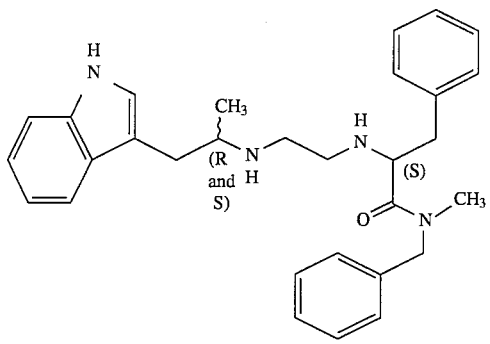

Prepare by the method of Example 23 using (S)-N-benzyl-N-methyl-2-[[(R and S)-2-(1H-indol-3-yl)-1-methyl-ethylamino]-N'-(t-butoxycarbonyl)-ethylamino]-3-phenyl-propionamide (0.192 g, 0.39 mmol) and purify by chromatography eluting with 5% methanol/dichloromethane and further purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound as a solid: TLC $R_f$=0.38 (silica gel, 10% methanol/dichloromethane). Elem. Anal. calculated for $C_{30}H_{36}N_3O.2C_2HF_3O_2.0.70H_2O$: C, 57.57; H, 5.60, N, 7.90. Found: C, 57.59; H, 5.74, N, 7.89.

EXAMPLE 30

(S)-N-Benzyl-N-methyl-2-[[[(S)-2-(1H-indol-3-yl)-1-carboxylic acid amide-ethylamino]-ethylamino]-3-phenyl-propionamide Scheme A, optional step c:

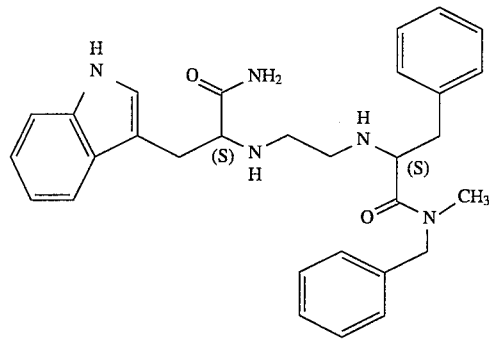

Prepare by the method of Example 23 using (S)-N-benzyl-N-methyl-2-[[(S)-2-(1H-indol-3-yl)-1-carboxylic acid amide-ethylamino]-N'-(t-butoxycarbonyl)-ethylamino]-3-phenyl-propionamide (0.36 g, 0.59 mmol) and purify by chromatography eluting with 5% methanol/dichloromethane to give the title compound: TLC $R_f$=0.56 (silica gel, 10% methanol/dichloromethane). HRMS calculated for $C_{30}H_{36}N_5O_2$ 498.2869. Found 498.2865.

EXAMPLE 31

(S)-N-(2-Methoxybenzyl)-N-methyl-2-[[(S)-2-(1H-indol-3-yl)-1-carboxymethyl-ethylamino]-ethylamino]-3-phenyl-propionamide Scheme A, optional step c:

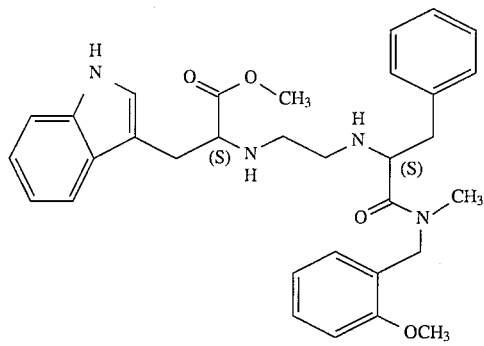

Prepare by the method of Example 23 using (S)-N-(2-methoxybenzyl)-N-methyl-2-[[(S)-2-(1H-indol-3-yl)-1-carboxymethyl-ethylamino]-N'-(t-butoxycarbonyl)-ethylamino]-3-phenyl-propionamide (0.15 g, 0.24 mmol) and purify by chromatography eluting with 10% methanol/dichloromethane to give the title compound. HRMS calculated for $C_{32}H_{39}N_4O_4$ 543.2971. Found 543.2980.

EXAMPLE 32

(S)-N-(3,4,5-Trimethoxybenzyl)-N-methyl-2-[[(S)-2-(1H-indol-3-yl)-1-carboxymethyl-ethylamino]ethylamino]-3-phenyl-propionamide Scheme A, optional step c:

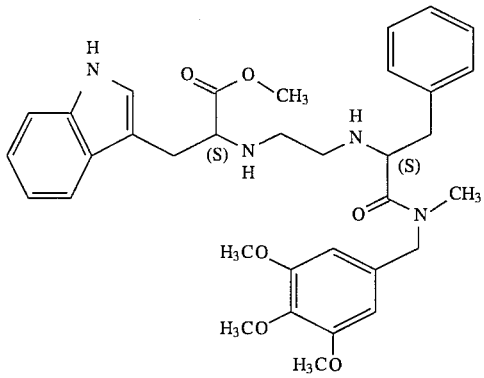

Prepare by the method of Example 23 using (S)-N-(3,4,5-trimethoxybenzyl)-N-methyl-2-[[(S)-2-(1H-indol-3-yl)-1-carboxymethyl-N'-(t-butoxycarbonyl)ethylamino]ethylamino]-3-phenyl-propionamide (0.48 g, 0.69 mmol) and purify by chromatography eluting with 3% methanol/dichloromethane to give the title compound. Elem. Anal. calculated for $C_{34}H_{42}N_4O_6$: C, 67.75; H, 7.02, N, 9.29. Found: C, 67.36; H, 6.98, N, 9.12.

EXAMPLE 33

(S)-N-Benzyl-N-methyl-2-[[(S)-2-(1H-indol-3-yl)-1-carboxymethyl-ethylamino]-ethylamino]-3-(naphth-2-yl)propionamide Scheme A, optional step c:

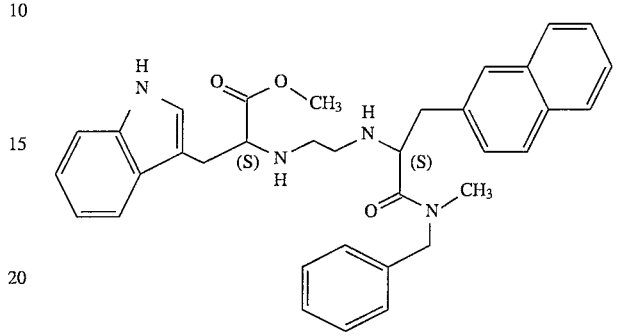

Prepare by the method of Example 23 using (S)-N-benzyl-N-methyl-2-[[(S)-2-(1H-indol-3-yl)-1-carboxymethyl-ethyl-ethylamino]-N'-(t-butoxycarbonyl)ethylamino]-3-(naphth-2-yl)-propionamide (0.34 g, 0.46 mmol) and purify by chromatography eluting with 5% methanol/dichloromethane to give the title compound: TLC $R_f$=0.75 (silica gel, 85% chloroform, 10% methanol, 5% acetic acid). HRMS calculated for $C_{35}H_{39}N_4O_3$ 563.3022. Found 563.2996.

EXAMPLE 34

(S)-N-(2-Methoxybenzyl)-N-methyl-2-[[(S)-2-(1H-indol-3-yl)-1-carboxymethyl-ethylamino]-ethylamino]-3-(naphth-2-yl)-propionamide Scheme A, optional step c:

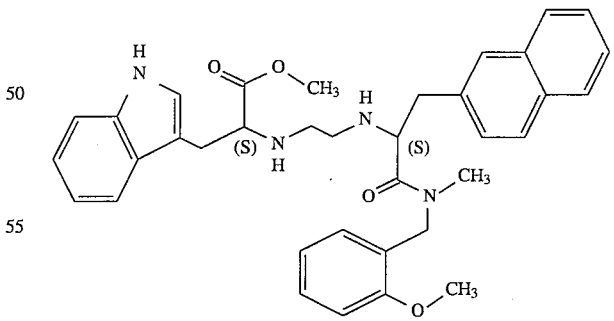

Prepare by the method of Example 23 using (S)-N-(2-methoxybenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide (1 mmol). Evaporate in vacuo. Chromatograph to give the title compound. HRMS calculated for $C_{32}H_{39}N_4O_4$ 543.2971. Found 543.2980.

EXAMPLE 35

(S)-N-(3,4-Dichlorobenzyl).-N-methyl-2-[[(S)-2-(1H-indol-3-yl)-1-carboxymethyl-ethylamino]-ethylamino]-3-(naphth-2-yl)-propionamide trifluoroacetic acid disalt Scheme A, optional step c:

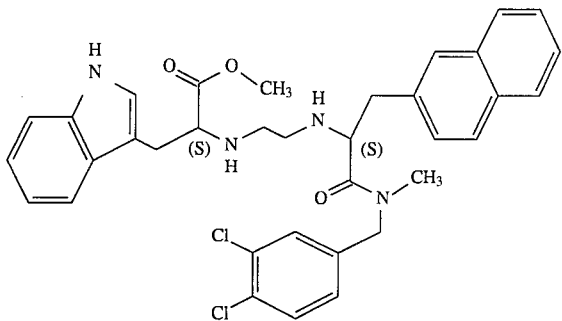

Prepare by the method of Example 23 using (S)-N-(3,4-dichlorobenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide (0.29 g, 0.39 mmol) and purify by chromatography eluting with 5% methanol/dichloromethane and further purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound: TLC $R_f$=0.57 (silica gel, 10% methanol/dichloromethane).

EXAMPLE 36

N-Methyl-N-[(S)-2-[[(S)-2-(1H-indol-37yl)-1-carboxymethyl-ethylamino]-ethylamino]-3-phenyl-propyl]-(3,4,5-trimethoxy)benzamide trifluoroacetic acid disalt Scheme A, optional step c:

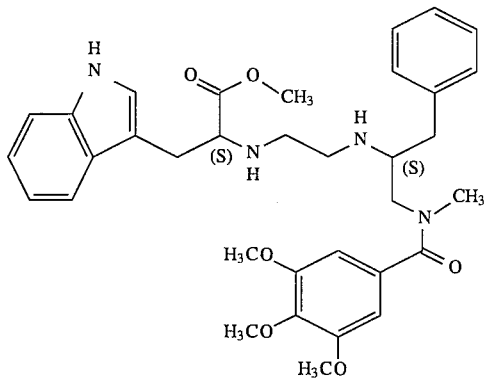

Prepare by the method of Example 23 using (S)-N-methyl-N-[2-[N'-(t-butoxycarbonyl)-2-oxo-ethylamino]-3-phenyl-propyl]-(3,4,5-trimethoxy)benzamide and purify by chromatography eluting with 5% methanol/dichloromethane and further purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound. HRMS calculated for $C_{34}H_{43}N_4O_6$ 603.3182. Found 603.3187.

EXAMPLE 37

N-Methyl-N-[(S)-2,[[(S),2-(1H-indol-3-yl)-1-carboxymethyl-ethylamino]-ethylamino]-3-phenyl-propyl]-benzamide trifluoroacetic acid disalt Scheme A optional step c:

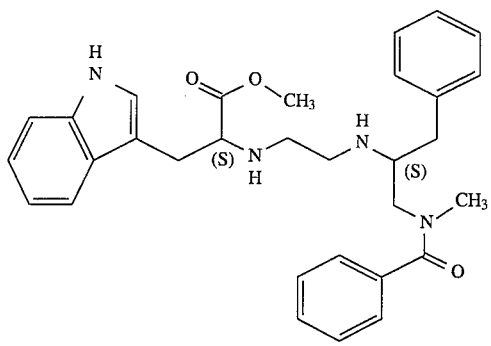

Prepare by the method of Example 23 using N-methyl-N-[(S)-2-[[(S)-2-(1H-indol-3-yl)-1-carboxymethyl-ethylamino]-N'-(t-butoxycarbonyl)-ethylamino]-3-phenyl-propyl]-benzamide (0.16 g, 0.26 mmol) and purify by chromatography eluting with 5% methanol/dichloromethane and further purify by HPLC (C-18 Vydac column, flow rate of 10 mL/minute: elute with a gradient 90% water (0.1% trifluoroacetic acid), 10% acetonitrile; to 50% water (0.1% trifluoroacetic acid), 50% acetonitrile over 25 minutes; and then to 100% acetonitrile over 25 minutes; to give the title compound. HRMS calculated for $C_{31}H_{37}N_4O_3$ 513.2865. Found 513.2872.

EXAMPLE 38

(S)-N-Methyl-N-[(S)-2-[[(S)-2-(1H-indol-3-yl)-1-carboxymethyl-ethylamino]-ethylamino]-3-phenyl-propyl]-benzimide Scheme A optional step c:

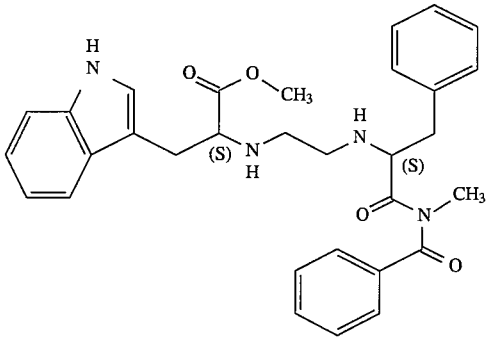

Prepare by the method of Example 23 using (S)-N-methyl-N-[(S)-2-[[(S)-2-(1H-indol-3-yl)-1-carboxymethyl-ethylamino ]-N'-(t-butoxycarbonyl)-ethylamino]-3-phenyl-propyl]-benzimide (0.26 mmol) and purify by chromatography to give the title compound.

EXAMPLE 39

(S)-N-Methyl-N-benzyl-N-[(S)-2-[(S)-2-(1H-indol-3-yl)-1-carboxymethyl-ethylamino]-ethylamino]-3-phenyl-propylamine Scheme A optional step c:

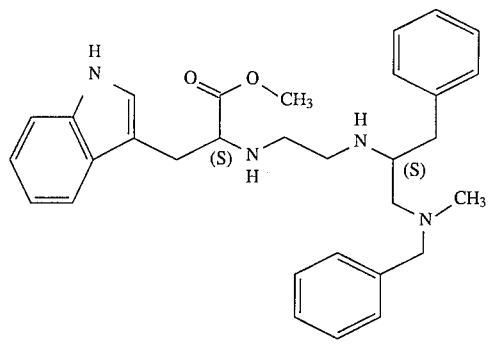

Prepare by the method of Example 23 using (S)-N-methyl-N-benzyl-N-[(S)-2-[(S)-2-(1H-indol-3-yl)-1-carboxymethyl-ethylamino]-N'-(t-butoxycarbonyl)-ethylamino]-3-phenyl-propylamine (0.40 mmol) and purify by chromatography to give the title compound.

EXAMPLE 40

(S)-N-Benzyl-N-methyl-2-[[(S)-2-[(1-(3-dimethylamino-propyl)-indol-3-yl)-1-carboxymethyl]-ethylamino]-ethylamino]-3-phenyl-propionamide trifluoroacetic acid trisalt Scheme A optional step c:

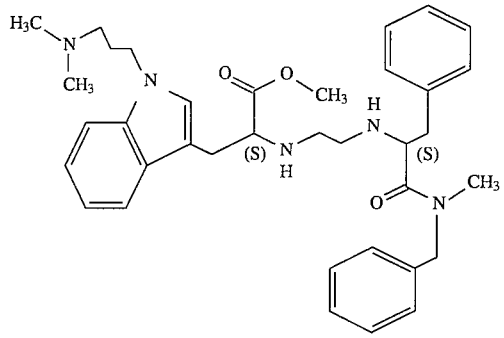

Prepare by the method of Example 23 using (S)-N-Benzyl-N-methyl-2-[[(S)-2-[(1-(3-dimethylamino-propyl)-indol-3-yl)-1-carboxymethyl]-N'''-(t-butoxycarbonyl)-ethylamino]-N'-(t-butoxycarbonyl)-ethylamino]-3-phenyl-propionamide (0.40 mmol) and purify by HPLC chromatography to give the title compound.

EXAMPLE 41

(S)-N-Benzyl-N-methyl-2-[[(S)-2-(1-carboxyethyl-indol-3-yl)-1-carboxymethyl-ethylamino]-ethylamino]-3-((naphth-2-yl))-propionamide trifluoroacetic acid disalt Scheme A optional step c:

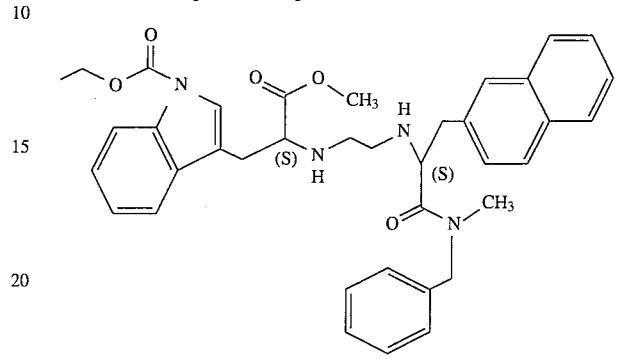

Prepare by the method of Example 23 using (S)-N-Benzyl-N-methyl-2-[[(S)-2-(1-carboxyethyl-indol-3-yl)-1-carboxymethyl-N'''-(t-butoxycarbonyl)-ethylamino]-N'-(t-butoxycarbonyl)-ethylamino]-3-((naphth-2-yl))-propionamide (0.40 mmol) and purify by chromatography to give the title compound.

EXAMPLE 42

(S)-N-Benzyl-N-methyl-2-[[(S)-2-(1H-indol-3-yl)-1-carboxy-ethylamino]-ethylamino]-3-phenyl-propionamide Scheme A, optional step b:

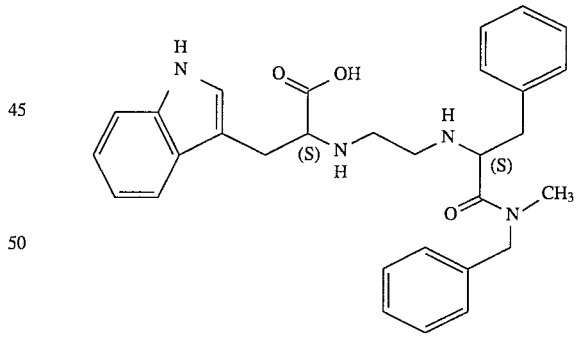

Combine (S)-N-benzyl-N-methyl-2-[[(S)-2-(1H-indol-3-yl)-1-carboxymethyl-ethylamino]ethylamino]-3-phenyl-propionamide (0.48 g, 0.93 mmol) and 1M sodium hydroxide (10 mL, 10 mmol) in ethanol (20 mL) and stir under an inert atmosphere for 18 hours. Dilute with water and extract with ethyl acetate, Acidify the aqueous layer with 1N hydrochloric acid and extract with ethyl acetate. Dry the organic layer over $MgSO_4$, filter and evaporate in vacuo to give the title compound as a solid: TLC $R_f$=0.43 (silica gel, 85% chloroform, 10% methanol, 5% acetic acid). HRMS calculated for $C_{30}H_{35}N_4O_3$ 499.2709. Found 499.2696.

EXAMPLE 43

(S)-N-Benzyl-N-methyl-2-[[(S)-2-(1H-indol-3-yl)-1-carboxymethyl-ethylamino]-propylamino]-3-phenyl-propionamide Scheme A, optional step c:

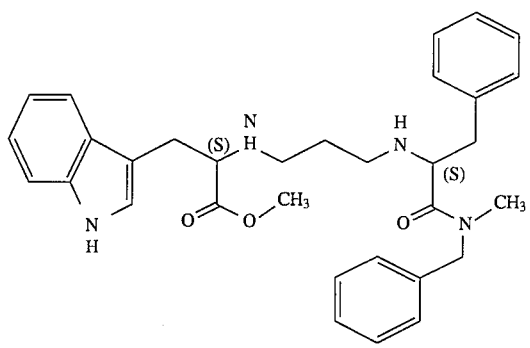

Prepare by the method of Example 23 using (S)-N-benzyl-N-methyl-2-[[(S)-2-(1H-indol-3-yl)-1-carboxymethyl-ethylamino]-N'-(t-butoxycarbonyl)-propylamino]-3-phenyl-propionamide (2 mmol). Purify by chromatography to give the title compound.

A general synthetic procedure is set forth in Scheme B for preparing the aldehyde of structure (3), in which $G_1$ is —$CH_2$— and $G_2$ is —C(O)—, used as a starting material in Scheme A. The reagents and starting materials are readily available to one of ordinary skill in the art. In Scheme B, all substituents, unless otherwise indicated, are as previously defined.

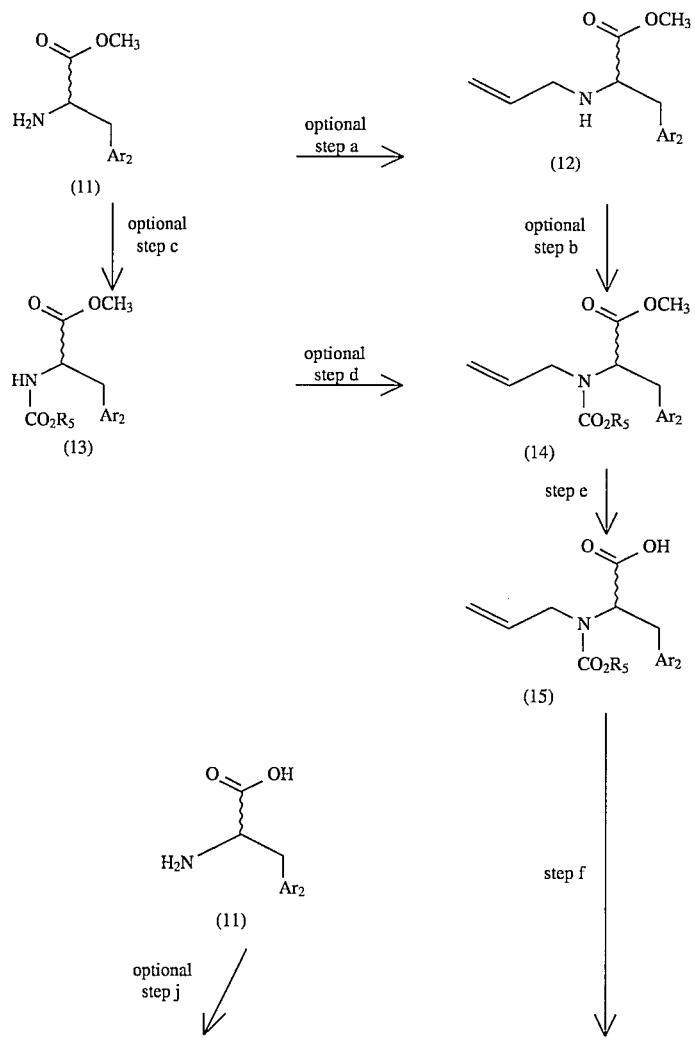

Scheme B

-continued
Scheme B

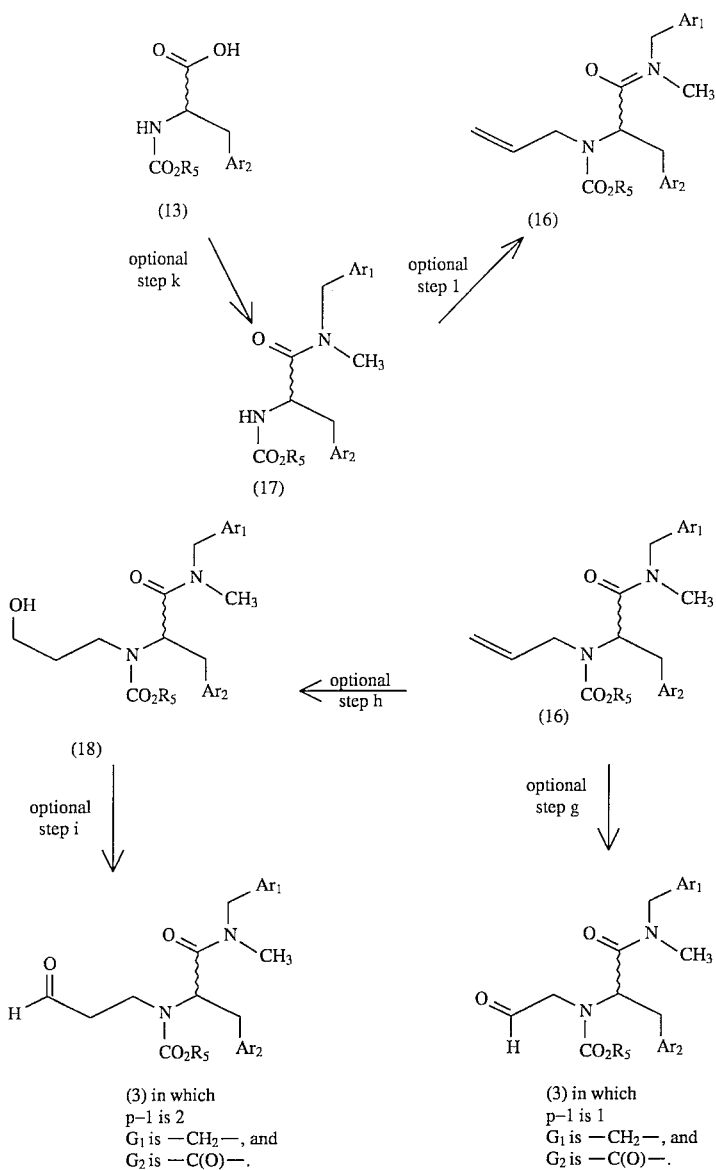

In Scheme B optional step a, an appropriate amino ester of structure (11) or a salt of an appropriate amino ester of structure (11) is allylated to give an allylamino ester of structure (12).

An appropriate amino ester of structure (11) is one in which the stereochemistry and $Ar_2$ are as desired in the final product of formula (1). An appropriate amino ester of structure (11) can also be one in which the stereochemistry is as desired in the final product of formula (1) and $Ar_2$ gives rise after deprotection to $Ar_2$ as desired in the final product of formula (1). An appropriate amino ester of structure (11) can also be one in which the stereochemistry gives rise after resolution to stereochemistry as desired in the final product of formula (1) and $Ar_2$ is as desired in the final product of formula (1). An appropriate amino ester of structure (11) can also be one in which the stereochemistry gives rise after resolution to stereochemistry as desired in the final product of formula (1) and $Ar_2$ gives rise after deprotection to $Ar_2$ as desired in the final product of formula (1).

The amino esters of structure (11) are readily prepared from α-amino-acids by methods known in the art. The required α-amino-acids can be obtained by methods known in the art or analogously known in the art, such as D. A. Evans, et al. *JACS* 112, 4011–4030 (1990); S. Ikegami et al. *Tetrahedron* 44, 5333–5342 (1988); W. Oppolzer et al. *Tet. Lets.* 30, 6009–6010 (1989); "Synthesis of Optically Active α-Amino-Acids", R. M. Williams (Pergamon Press, Oxford 1989); M. J. O'Donnell ed: "α-Amino-Acid Synthesis" *Tetrahedron* Symposia in print, No. 33, *Tetrahedron* 44, No. 17 (1988); U. Schöllkopf, *Pure Appl. Chem.* 55, 1799 (1983); U. Hengartner et al. *JOC* 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *JACS* 110, 8520–8525 (1988).

For example, an appropriate amino ester of structure (11) or a salt of an appropriate amino ester of structure (11) is contacted with from 1 to 3 molar equivalents of allyl bromide or allyl chloride. The allyl bromide or allyl chloride is preferably added portionwise over the course of the reaction. When a salt of an appropriate amino ester of structure (11) is used the reaction is carried out in the presence of an equimolar amount of a suitable base, such as triethyl amine or diisopropylethyl amine. The reaction is carried out in a suitable solvent, such as tetrahydrofuran. Generally, the reaction is carried out at temperatures of from 0° C. to the refluxing temperature of the solvent. Generally, the reactions require from 1 to 72 hours. The product can be isolated and purified by techniques well known in the art, such as extraction, evaporation, chromatography, and recrystallization.

In Scheme B, optional step b, an allylamino ester of structure (12) or as salt of an allylamino ester of structure (12) the allyl amino group is converted to a carbamate with an appropriate carbamate forming reagent to give a compound of structure (14).

An appropriate carbamate forming reagent is one which transfers to an amine the group —$CO_2R_5$, such as methyl chloroformate, ethyl chloroformate, propyl chloroformate, iso-butyl chloroformate, benzyl chloroformate, and di-t-butyl dicarbonate, etc.

For example, an allylamino ester of structure (12) or as salt of an allylamino ester of structure (12) is contacted with a reagent which transfers to an amine the group —$CO_2R_5$. When a salt of an allylamino ester of structure (12) is used the reaction is carried out in the presence of an equimolar amount of a suitable base, such as triethylamine or diisopropylethylamine. When the reaction is carried out using a carbamate forming reagent which liberates acid as the carbamate is formed, such as methyl chloroformate, ethyl chloroformate, propyl chloroformate, iso-butyl chloroformate, etc, an equimolar amount of a suitable base, such as triethylamine or diisopropylethylamine is used to neutralize the acid which is liberated. The reaction is carried out in a suitable solvent, such as tetrahydrofuran, dimethylformamide, ethyl acetate, or dimethylformamide/ethyl acetate mixtures. Generally, the reactions are carried out at ambient temperature. The product can be isolated and purified by techniques well known in the art, such as extraction, evaporation, chromatography, and recrystallization.

Alternately, a carbamate of structure (14) in which $R_5$ is t-butyl may be prepared by Scheme B optional steps c and d.

In Scheme B, optional step c, an appropriate amino ester of structure (11) or a salt of an appropriate amino ester of structure (11) is contacted with an appropriate carbamate forming reagent to give a compound of structure (13).

An appropriate carbamate forming reagent for the use of this alternate route for preparing compounds of structure (14) is one which transfers an t-butyl carbamate, such as di-t-butyl dicarbonate.

An appropriate amino ester of structure (11) or a salt of an appropriate amino ester of structure (11) is one in which the stereochemistry and $Ar_2$ are as desired in the product of formula (1) or can be one which gives rise after resolution or deprotection to stereochemistry or $Ar_2$ as desired in the final product of formula (1).

For example, an amino ester of structure (11) or as salt of an amino ester of structure (11) is contacted with a reagent which transfers a t-butoxycarbonyl group, such as di-t-butyl dicarbonate. When a salt of an amino ester of structure (11) is used the reaction is carried out in the presence of an equimolar amount of a suitable base, such as triethyl amine or diisopropylethyl amine. The reaction is carried out in a suitable solvent, such as dimethylformamide, ethyl acetate, or dimethylformamide/ ethyl acetate mixtures. Generally, the reactions are carried out at ambient temperature. The product can be isolated and purified by techniques well known in the art, such as extraction, evaporation, chromatography, and recrystallization.

In Scheme B, optional step d, a carbamate ester of structure (13) in which $R_5$ is t-butyl is allylated to give an allyl-carbamate ester of structure (14) in which $R_5$ is t-butyl.

For example, a carbamate ester of structure (13) is contacted with allyl bromide or allyl chloride. The reaction is carried out in the presence of a suitable base, such as sodium hydride or sodium bis(trimethylsilyl)amide. The reaction is carried out in a suitable solvent, such as tetrahydrofuran, dimethylformamide, or tetrahydrofuran/dimethylformamide mixtures. The reaction is carried out at temperature of from 0° C. to the reflux temperature of the solvent. The product can be isolated and purified by techniques well known in the art, such as extraction, evaporation, chromatography, and recrystallization.

In Scheme B, step e, an allyl-carbamate ester of structure (14) is hydrolyzed to give an allyl-carbamate acid of structure (15).

For example, an allyl-carbamate ester of structure (14) is contacted with a suitable base, such as sodium hydroxide, lithium hydroxide, or potassium hydroxide. The reaction is carried out in a suitable solvent, such as methanol, ethanol, water, methanol/water mixtures, ethanol/water mixtures, or tetrahydrofuran/water mixtures. Generally, the reaction is carried out at ambient temperature. Generally, the reaction requires from 2 to 72 hours. The product can be isolated and purified by techniques well known in the art, such as acidification, filtration, extraction, evaporation, and recrystallization.

In Scheme B step f, an allyl-carbamate acid of structure (15) undergoes an amidation reaction with an appropriate amine to give an allyl-carbamate amide of structure (16).

An appropriate amine of structure $HN(CH_3)CH_2Ar_1$ is one in which the group $Ar_1$ is as desired in the product of formula (1) or give rise after deprotection to $Ar_1$ as desired in the final product of formula (1).

An amidation reaction may proceed through an activated intermediate, such as a mixed anhydride or a (O)-hydroxybenzotriazole, which may be prepared but is not necessarily isolated before the addition of an appropriate amine, $HN(CH_3)CH_2Ar_1$.

For example, an allyl-carbamate acid of structure (15) is contacted with 1.2 to 1.7 equivalents of a suitable base, such as N-methylmorpholine, in a suitable solvent, such as tetrahydrofuran. Generally, the reaction mixture is cooled to a temperature of between –50° C. and 0° C. with –25° C. to –20° C. being preferred, before the addition of 1.2 to 1.7 equivalents of isobutyl chloroformate. The reaction is allowed to stir for about 30 minutes to 3 hours to allow for the formation of the mixed anhydride, an activated intermediate. While maintaining the temperature at between –50° C. and 0° C. an appropriate amine of structure $HN(CH_3)CH_2Ar_1$ is added. The reaction may, after the addition of amine is complete, be warmed to room temperature. The reaction requires from 2 to 48 hours. The product can be isolated and purified by techniques well known in the art, such as extraction, evaporation, chromatography, and recrystallization.

Alternatively, for example, an allyl-carbamate acid of structure (15) is contacted with a slight molar excess of an appropriate amine, $HN(CH_3)CH_2Ar_1$, and 1-hydroxybenzotriazole hydrate in the presence of a slight molar excess of a coupling agent, such as dicyclohexylcarbodiimide or 1-(3-dimethylaminopropyl)-3-ethylcarbodiimide. The reaction is carried out in the presence of a suitable base, such as diisopropylethylamine. The reaction is carried out in a suitable solvent, such as dimethylformamide, dichloromethane, or chloroform. The product can be isolated and purified by techniques well known in the art, such as extraction, evaporation, chromatography, and recrystallization.

Alternately, an allyl-carbamate amide of structure (16) can be prepared from an amino acid according to Scheme B optional steps j, k, and l.

In Scheme B, optional step j, an appropriate amino acid of structure (11) or a salt of an appropriate amino acid of structure (11) is contacted with an appropriate carbamate forming reagent to give a compound of structure (17).

An appropriate carbamate forming reagent for the use of this alternate route for preparing compounds of structure (13) is one which transfers a t-butyl carbamate, such as di-t-butyl dicarbonate.

An appropriate amino acid of structure (11) or a salt of an appropriate amino acid of structure (11) is one in which the stereochemistry and $Ar_2$ are as desired in the product of formula (1) or is one which gives rise after resolution or deprotection to stereochemistry or $Ar_2$ as desired in the final product of formula (1).

For example, an appropriate amino acid of structure (11) or a salt of an appropriate amino acid of structure (11) is contacted with a reagent which transfers a t-butoxycarbonyl group, such as di-t-butyl dicarbonate. The reaction is carried out in the presence of an equimolar amount of a suitable base, such as triethyl amine or diisopropylethyl amine. When a salt of an appropriate amino acid of structure (11) is used an additional equimolar amount of a suitable base is used. The reaction is carried out in a suitable solvent, such as dimethylformamide, ethyl acetate, or dimethylformamide/ethyl acetate mixtures. Generally, the reactions are carried out at ambient temperature. The product can be isolated and purified by techniques well known in the art, such as extraction, evaporation, chromatography, and recrystallization.

In Scheme B, step k, a t-BOC protected amino acid of structure (13) undergoes an amidation reaction with an appropriate amine, as generally taught in Scheme B, step f, to give a t-BOC protected amino amide of structure (17).

An appropriate amine of structure $HN(CH_3)CH_2Ar_1$ is one in which $Ar_1$ is as desired in the product of formula (1) or give rise after deprotection to $Ar_1$ as desired in the final product of formula (1).

In Scheme B, optional step l, a t-BOC protected amino amide of structure (17) is allylated as generally taught in Scheme B, optional step d, to give an allyl-carbamate amide of structure (16) in which $R_5$ is t-butyl.

In Scheme B, optional step g, an allyl-carbamate amide of structure (16) is converted to an aldehyde of structure (3) in which p-1 is 1. An allyl-carbamate amide of structure (16) may be converted to an aldehyde of structure (3) in which p-1 is 1 by either; ozonolysis in the presence of methanol followed by a reductive work-up, or an osmium tetraoxide mediated formation of an intermediate diol followed by oxidative cleavage with lead tetraacetate or sodium metaperiodate.

For example, an allyl-carbamate amide of structure (16) is contacted with ozone in the presence of methanol. The reaction is carried out in a suitable solvent, such as dichloromethane. Generally, the reaction is carried out at a temperature of from −100° C. to −60° C., with −70° C. being preferred. The reaction is worked-up reductively by the addition of a suitable reducing agent, such as tributylphosphine or dimethyl sulfide. The product may be isolated from the reaction zone by evaporation and may be used without further purification. The product may be purified by techniques well known in the art, such as chromatography and recrystallization.

Alternatively, an aldehyde of structure (3) can be prepared by oxidation of an allyl-carbamate amide of structure (16) to an intermediate diol followed by treatment with lead tetraacetate.

For example, an allyl-carbamate amide of structure (16) is contacted with osmium tetraoxide to give an intermediate diol. The reaction may be carried out using a 0.01 to 0.05 molar equivalents of osmium tetraoxide and a slight molar excess of an oxidant, such as N-methylmorpholine-N-oxide or t-butyl hydroperoxide. The reaction is carried out in a solvent, such as acetone/water mixtures. Generally, the reaction is carried out at ambient temperature and requires from 1 to 48 hours. The reaction mixture is added to a saturated solution of sodium bisulfite or sodium thiosulfate and the intermediate diol is isolated by extraction and evaporation and used without further purification. The intermediate diol is contacted with a slight molar excess of lead tetraacetate. The reaction is carried out in a solvent, such as chloroform. The reaction is carried out at ambient temperature and requires from 30 minutes to 8 hours. The product may be isolated from the reaction zone by extraction and evaporation and may be used without further purification. The product may be purified by techniques well known in the art, such as chromatography and recrystallization.

In Scheme B, optional step h, an allyl-carbamate amide of structure (16) is contacted with an appropriate borane reagent followed oxidation with peroxide to give an alcohol of structure (18).

An appropriate borane reagent, such as dicyclohexylborane is one that reacts with an allyl-carbamate amide of structure (16) in a way that hydrogen peroxide oxidation gives an alcohol of structure (18).

For example, an allyl-carbamate amide of structure (16) is contacted with an appropriate borane reagent, such as dicyclohexylborane. The reaction is carried out in a suitable solvent, such as tetrahydrofuran. The reaction mixture is maintained at a temperature of from −20° C. to 10° C. during the combining of reactants. The reaction is carried out at ambient temperature. The borane formation reaction requires form 1 to 8 hours. A pH 7 phosphate buffer in a suitable solvent, such as ethanol is added before the addition of an excess of hydrogen peroxide. Generally, the oxidation requires from 8 to 48 hours and is carried out at ambient temperature. The product can be isolated and purified by techniques well known in the art, such as extraction, evaporation, chromatography, and recrystallization.

In Scheme B, optional step i, an alcohol of structure (18) is oxidized to give an aldehyde of structure (3) in which p-1 is 2.

For example, two molar equivalents of dimethyl sulfoxide are added dropwise to a solution of oxalyl chloride, pyridine sulfur trioxide complex, or trifluoroacetic anhydride in dichloromethane, at approximately −60° C. After the addition is complete, the reaction is stirred for approximately two minutes. A molar equivalent of an alcohol of structure (18) as a solution in dichloromethane is added dropwise. After the addition is complete the reaction mixture is stirred for approximately forty minutes, then a 3-fold to 5-fold excess of triethylamine is added. The reaction mixture is allowed to stir with warming to ambient temperature over 1 hour to 5 hours. The product can be isolated and purified by techniques well known in the art, such as extraction, evaporation, chromatography, and recrystallization.

The following examples present typical syntheses as described in Scheme B. These examples and preparations are understood to be illustrative only and are not intended to limit the scope of the invention in any way.

EXAMPLE 44

2-(Methoxy)benzylmethylamine

Starting material for Examples 50 and 55;

Combine o-anisoyl chloride (2-methoxybenzoyl chloride) (2.9 g, 17.0 mmol) and tetrahydrofuran (170 mL) and cool to 0° C. Add diisopropylethylamine (5.92 mL, 34 mmol). Add methylamine hydrochloride (1.26 g, 18.7 mmol). Allow to stir for 1 hour and concentrate in vacuo. Chromatograph on silica gel eluting sequentially with 50% ethyl acetate/hexane to give N-methyl-2-methoxybenzamide: TLC $R_f$=0.45 (silica gel, 50% ethyl acetate/hexane).

Combine N-methyl-2-methoxybenzamide (1.55 g, 9.36 mmol) and tetrahydrofuran (100 mL) and heat to reflux. Slowly, add dropwise a solution of borane dimethyl sulfide complex (28.1 mL, 2.0M in tetrahydrofuran, 56.2 mmol). Heat to reflux for 1 hour after the addition is complete. Cool to ambient temperature and concentrate in vacuo to obtain a residue. Cool the residue to 0° C. Slowly, add 6M hydrochloric acid solution. After the addition is complete, heat the mixture to reflux for 1 hour. Cool to 0° C., add 6M sodium hydroxide solution until the pH is 7. Extract the reaction mixture with ethyl acetate. Dry the organic layer over MgSO$_4$, filter, and evaporate in vacuo to give the title compound.

EXAMPLE 45

3,4,5-(Trimethoxy)benzylmethylamine

Starting material for Example 51;

Combine 3,4,5-trimethoxybenzoyl chloride (2.9 g, 17.0 mmol) and tetrahydrofuran (170 mL) and cool to 0° C. Add diisopropylethylamine (5.92 mL, 34 mmol). Add methylamine hydrochloride (1.26 g, 18.7 mmol). Allow to stir for 1 hour and concentrate in vacuo. Chromatograph on silica gel eluting sequentially with 50% ethyl acetate/hexane to give N-methyl-3,4,5-trimethoxybenzamide: TLC $R_f$=0.45 (silica gel, 50% ethyl acetate/hexane).

Combine N-methyl-3,4,5-trimethoxybenzamide (1.55 g, 9.36 mmol) and tetrahydrofuran (100 mL) and heat to reflux. Slowly, add dropwise a solution of borane dimethyl sulfide complex (28.1 mL, 2.0M in tetrahydrofuran, 56.2 mmol). Heat to reflux for 1 hour after the addition is complete. Cool to ambient temperature and concentrate in vacuo to obtain a residue. Cool the residue to 0° C. Slowly, add 6M hydrochloric acid solution. After the addition is complete, heat the mixture to reflux for 1 hour. Cool to 0° C., add 6M sodium hydroxide solution until the pH is 7. Extract the reaction mixture with ethyl acetate. Dry the organic layer over MgSO$_4$, filter, and evaporate in vacuo to give the title compound.

EXAMPLE 46

(S)-2-Allylamino-3-phenyl-propionic acid methyl ester

Scheme B, optional step a:

Combine (S)-2-amino-3-phenyl-propionic acid methyl ester hydrochloride salt ((S)-phenylalanine methyl ester hydrochloride salt) (8.63 g, 40.0 mmol), diisopropylethylamine (6.8 mL, 40.0 mmol), and allyl bromide (1.8 mL, 20.0 mmol) in THF (200 mL). Stir under an inert atmosphere for 16 hours. Add allyl bromide (1.8 mL, 20.0 mmol) and stir for an additional 24 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting with 30% ethyl acetate/hexane to give the title compound: TLC $R_f$=0.43 (silica gel, 30% ethyl acetate/hexane).

EXAMPLE 47

(S)-2-[N-(t-Butoxycarbonyl)-allylamino]-3-phenyl-propionic acid methyl ester Scheme B, optional step b:

Combine (S)-2-allylamino-3-phenyl-propionic acid methyl ester (6.62 g, 30.4 mmol) and di-t-butyl dicarbonate (7.29 g, 33.5 mmol) in DMF/ethyl acetate (30 mL/30 mL). Stir for 16 hours under an inert atmosphere. Dilute the reaction mixture with ethyl acetate and extract with water. Separate the layers, dry the organic layer over MgSO$_4$, filter, and evaporate in vacuo. Chromatograph on silica gel eluting with 10% ethyl acetate/hexane to give the title compound.

EXAMPLE 48

(S)-2-[N-(t-Butoxycarbonyl)-allylamino]-3-phenyl-propionic acid

Scheme B, step e:

Combine (S)-2-[N-(t-butoxycarbonyl)-allylamino-3-phenyl-propionic acid methyl ester (0.32 g, 1.0 mmol) and 1M sodium hydroxide (10 mL, 10 mmol) in ethanol (10 mL). Stir for 4 hours. Acidify the reaction mixture with 1M hydrochloric acid and extract with ethyl acetate. Separate the layers, dry the organic layer over MgSO$_4$, filter, and evaporate in vacuo. Chromatograph on silica gel eluting with 3% methanol/dichloromethane to give the title compound: TLC $R_f$=0.40 (silica gel, 5% methanol/dichloromethane).

EXAMPLE 49

(S)-N-Benzyl-N-methyl-2-[N-(t-butoxycarbonyl)-allylamino]-3-phenyl-propionamide Scheme B, step f:

Combine (S)-2-[N-(t-butoxycarbonyl)-allylamino-3-phenyl-propionic acid (11.1 g, 36.35 mmol), and THF (360 mL). Cool to −22° C. Add N-methylmorpholine (7.09 mL, 54.53 mmol) and then stir for 10 minutes. Add isobutyl chloroformate (7.09 mL, 54.53 mmol) and stir for 30 minutes at −22° C. Add N-methyl-N-benzylamine (7.09 mL, 54.53 mmol). Allow to warm to ambient temperature and stir for 2 hours. Dilute the reaction mixture with ethyl acetate and extract with water. Separate the layers, dry the organic layer over MgSO$_4$, filter, and evaporate in vacuo. Chromatograph on silica gel eluting with 10% ethyl acetate/hexane to give the title compound.

EXAMPLE 50

(S)-N-(2-Methoxybenzyl)-N-methyl-
2-[N'-(t-butoxycarbonyl)-allylamino]-
3-phenyl-propionamide Scheme B, step g:

Combine (S)-2-[N-(t-butoxycarbonyl)-allylamino]-3-phenyl-propioic acid (1.59 g, 5.20 mmol), (2-methoxybenzyl)methylamine (0.79 g, 5.20 mmol), 1-(3-dimethylaminopropyl)-3-ethylcarbodiimide hydrochloride (1.12 g, 5.72 mmol), 1-hydroxybenzotriazole (0.38 g, 2.52 mmol ), and diisopropylethylamine (1.34 mL, 6.5 mmol) in dichloromethane (50 mL)and stir for 18 hours. Dilute with ethyl acetate and extract with 1M hydrochloric acid, a saturated aqueous solution of sodium bicarbonate and a saturated aqueous solution of sodium chloride. Dry the separated organic layer over $MgSO_4$, filter and evaporate in vacuo. Chromatograph on silica gel eluting sequentially with 5% ethyl acetate/hexane and 10% ethyl acetate/hexane to give the title compound: TLC $R_f$=0.55 (silica gel, 30% ethyl acetate/hexane).

EXAMPLE 51

(S)-N-(3,4,5-Trimethoxybenzyl)-N-methyl-
2-[N'-(t-butoxycarbonyl)-allylamino]-
3-phenyl-propionamide Scheme B, step g:

Combine (S)-2-[N-(t-butoxycarbonyl)-allylamino]-3-phenyl-propioic acid (0.91 g, 2.97 mmol), (3,4,5-trimethoxy)-benzylmethylamine (0.63 g, 2.97 mmol), 1-(3-dimethylaminopropyl)-3-ethylcarbodiimide hydrochloride (0.63 g, 3.27 mmol), 1-hydroxybenzotriazole (0.349 g, 3.27 mmol), and diisopropylethylamine (0.77 mL, 6.27 mmol) in dichloromethane (30 mL) and stir for 18 hours. Dilute with ethyl acetate and extract with 1M hydrochloric acid, a saturated aqueous solution of sodium bicarbonate and a saturated aqueous solution of sodium chloride. Dry the separated organic layer over $MgSO_4$, filter and evaporate in vacuo. Chromatograph on silica gel eluting with 30% ethyl acetate/hexane to give the title compound: TLC $R_f$=0.30 (silica gel, 30% ethyl acetate/hexane).

EXAMPLE 52

(S)-2-[N-(t-Butoxycarbonyl)amino]-
3-(naphth-2-yl)-propionic acid

Scheme B, optional step j:

Combine (S)-2-amino-3-(naphth-2-yl)-propionic acid ((S)-(2-napthyl)-alanine) (2.0 g, 9.29 mmol) and di-t-butyl dicarbonate (2.23 g, 10.22 mmol) in 1/1 DMF/ethyl acetate (200 mL). Add diisopropylethylamine (2.0 mL) to solubilized the (S)-2-amino-3-(2-napthyl)-propionic acid and stir for 18 hours. Dilute with ethyl acetate and extract with 1M hydrochloric acid solution. Dry the separated organic layer over $MgSO_4$, filter and evaporate in vacuo to give the title compound: TLC $R_f$=0.47 (silica gel, 10% methanol/dichloromethane).

EXAMPLE 53

(S)-N-Benzyl-N-methyl-2-[N'-(t-butoxycarbonyl) amino]-3-(naphth-2-yl)-propionamide Scheme B, optional step k:

Combine (S)-2-[N-(t-butoxycarbonyl)amino]-3-(naphth-2-yl)-propionic acid (2.92 g, 9.3 mmol), 1-(3-dimethylaminopropyl)-3-ethylcarbodiimide hydrochloride (1.96 g, 10.22 mmol), 1-hydroxybenzotriazole (1.38 g, 10.22 mmol), N-methyl-N-benzylamine (9.3 mmol), and diisopropylethylamine (1.78 mL, 10.22 mmol) in dichloromethane (100 mL) and stir for 18 hours. Dilute with ethyl acetate and extract with 1M hydrochloric acid, a saturated aqueous solution of sodium bicarbonate and a saturated aqueous solution of sodium chloride. Dry the separated organic layer over $MgSO_4$, filter and evaporate in vacuo. Chromatograph on silica gel eluting with 20% ethyl acetate/hexane to give the title compound: TLC $R_f$=0.29 (silica gel, 20% ethyl acetate/hexane).

EXAMPLE 54

(S)-N-(3,4-Dichlolobenzyl)-N-methyl-
2-[N'-(t-butoxycarbonyl)amino]-
3-(naphth-2-yl)-propionamide Scheme B, optional step k:

Combine (S)-2-[N-(t-butoxycarbonyl)amino]-3-(naphth-2-yl)-propionic acid (1.23 g, 3.93 mmol), 1-(3-dimethylaminopropyl)-3-ethylcarbodiimide hydrochloride (0.435 g, 2.2 mmol), 1-hydroxybenzotriazole (0.297 g, 2.2 mmol), N-methyl-N-(3,4-dichlorobenzyl)amine (0.382, 2.0 mmol), and diisopropylethylamine (0.53 mL, 2.2 mmol) in dichloromethane (20 mL) and stir for 72 hours. Dilute with ethyl acetate and extract with 1M hydrochloric acid, a saturated aqueous solution of sodium bicarbonate and a saturated aqueous solution of sodium chloride. Dry the separated organic layer over $MgSO_4$, filter and evaporate in vacuo. Chromatograph on silica gel eluting with 10% ethyl acetate/ hexane to give the title compound.

EXAMPLE 55

(S)-N-(2-Methoxybenzyl)-N-methyl-
2-[N'-(t-butoxycarbonyl)amino]-3-(naphth-2-yl)-
propionamide Scheme B, optional step k:

Combine (S)-2-[N-(t-butoxycarbonyl)amino]-3-(naphth-2-yl)-propionic acid (1.89 g, 6.0 mmol), (2-methoxybenzyl)methylamine (1.67 g, 11.1 mmol), 1-(3-dimethylaminopropyl)-3-ethylcarbodiimide hydrochloride (1.30 g, 6.6 mmol), 1-hydroxybenzotriazole (0.89 g, 6.6 mmol), and diisopropylethylamine (1.59 mL, 6.6 mmol) in dichloromethane (60 mL) and stir for 18 hours. Dilute with ethyl acetate and extract with 1M hydrochloric acid, a saturated aqueous solution of sodium bicarbonate and a saturated aqueous solution of sodium chloride. Dry the separated organic layer over $MgSO_4$, filter and evaporate in vacuo to give the title compound as a colorless oil.

EXAMPLE 56

(S)-N-Benzyl-N-methyl-2-[N'-(t-butoxycarbonyl)-
allylamino]-3-(naphth-2-yl)-propionamide Scheme B, optional step 1:

Combine (S)-N-benzyl-N-methyl-2-[N'-(t-butoxycarbonyl)amino]-3-(naphth-2-yl)-propionamide (3.3 g, 7.9 mmol) and THF/DMF (70 mL/7 mL) and cool in an ice bath at 0° C. Add sodium hydride (0.42 g, 17.38 mmol) and allyl bromide (4.1 mL, 47.4 mmol). Allow the reaction to warm to ambient temperature and then heat to reflux for 18 hours. Pour the reaction mixture into a saturated aqueous solution of ammonium chloride. Separate the layers and extract the aqueous layer with dichloromethane. Combine the organic layers. Dry over $MgSO_4$, filter, and evaporate in vacuo. Chromatograph on silica gel eluting sequentially with 10% ethyl acetate/hexane and 20% ethyl acetate/hexane to give the title compound: TLC $R_f$=0.59 (silica gel, 20% ethyl acetate/hexane).

EXAMPLE 57

(S)-N-(3,4-Dichlorobenzyl)-N-methyl-
2-[N'-(t-butoxycarbonyl)-allylamino]-
3-(naphth-2-yl)-propionamide Scheme B, optional step 1:

Combine (S)-N-(3,4-dichlorobenzyl)-N-methyl-2-[N'-(t-butoxycarbonyl)amino]-3-(naphth-2-yl)-propionamide (0.48 g, 0.99 mmol) and THF/DMF (9 mL/1 mL) and cool in an ice bath at 0° C. Add sodium hydride (0.048 g, 2.0 mmol) and allyl bromide (0.52 mL). Allow the reaction to warm to ambient temperature and then heat to reflux for 18 hours. Pour the reaction mixture into a saturated aqueous solution of ammonium chloride. Separate the layers and extract the aqueous layer with dichloromethane. Combine the organic layers. Dry over $MgSO_4$, filter, and evaporate in vacuo. Chromatograph on silica gel eluting sequentially with 10% ethyl acetate/hexane and 20% ethyl acetate/hexane to give the title compound as a solid.

EXAMPLE 58

(S)-N-(2-Methoxybenzyl)-N-methyl-
2-[N'-(t-butoxycarbonyl)-allylamino]-
3-(naphth-2-yl)-propionamide Scheme B, optional step 1:

Combine (S)-N-(2-methoxybenzyl)-N-methyl-2-[N'-(t-butoxycarbonyl)amino]-3-(naphth-2-yl)-propionamide (0.63 g, 1.41 mmol) and THF/DMF (15 mL/5 mL) and cool in an ice bath at 0° C. Add sodium hydride (0.067 g, 2.82 mmol) and allyl bromide (0.73 mL, 8.46 mmol). Allow the reaction to warm to ambient temperature and then heat to reflux for 18 hours. Pour the reaction mixture into a saturated aqueous solution of ammonium chloride. Separate the layers and extract the aqueous layer with dichloromethane. Combine the organic layers. Dry over $MgSO_4$, filter, and evaporate in vacuo. Chromatograph on silica gel eluting with 10% ethyl acetate/hexane to give the title compound: TLC $R_f$=0.55 (silica gel, 20% ethyl acetate/hexane).

EXAMPLE 59

(S)-N-Benzyl-N-methyl-2-[N'-(t-butoxycarbonyl)-
2-oxo-ethylamino]-3-phenyl-propionamide Scheme B, Step g:

Combine (S)-N-benzyl-N-methyl-2-[N'-(t-butoxycarbonyl)-allylamino]-3-phenyl-propionamide (10.04 g, 24.5 mmol), and pyridine (0.13 ml) in dichloromethane/methanol (300 mL/30 mL). Cool to −78° C. Pass ozonized oxygen through the solution until a persistent light blue color is obtained. Pass nitrogen through the solution until the blue color dissipates. Add dimethyl sulfide (55 mL). Allow the reaction mixture to warm to ambient temperature and stir for 16 hours. Concentrate in vacuo to obtain a residue. Dilute the residue with ethyl acetate and extract with water. Separate the layers, dry the organic layer over $MgSO_4$, filter, and evaporate in vacuo. Chromatograph on silica gel eluting with 10% ethyl acetate/hexane to give the title compound: TLC $R_f$=0.53 (silica gel, 10% ethyl acetate/hexane).

EXAMPLE 60

(S)-N-(2-Methoxybenzyl)-N-methyl-
2-[N'-(t-butoxycarbonyl)-2-oxo-ethylamino]-
3-phenyl-propionamide Scheme D, step g:

Combine (S)-N-(2-methoxybenzyl)-N-methyl-2-[N'-(t-butoxycarbonyl)-allylamino]-3-phenyl-propionamide (0.66 g, 1.52 mmol), N-methylmorpholine-N-oxide (0.20 g, 1.67 mmol), acetone (5 mL), and water (5 mL). Add osmium tetraoxide (0.78 mL, 0.04M in THF, 0.032 mmol) and stir under an inert atmosphere for 18 hours. Pour the reaction mixture into a saturated solution of sodium bisulfite and extract the intermediate diol into ethyl acetate. Dry the separated organic layer over $MgSO_4$, filter, and evaporate in vacuo to give the crude diol which is used without further purification. Dissolve the crude diol in chloroform (10 mL). Add a solution of lead tetraacetate (0.74 g, 1.67 mmol) in chloroform (10 mL). Stir for 30 minutes and then pour the reaction mixture into a saturated solution of sodium bicarbonate. Extract with dichloromethane and separate the organic layer. Dry the separated organic layer over $MgSO_4$, filter and evaporate in vacuo to give the title compound which may be used without further purification.

EXAMPLE 61

(S)-N-(3,4,5-Trimethoxybenzyl)-N-methyl-
2-[N'-(t-butoxycarbonyl)-2-oxo-ethylamino]-
3-phenyl-propionamide Scheme B, step g:

Combine (S)-N-(3,4,5-trimethoxybenzyl)-N-methyl-2-[N'-(t-butoxycarbonyl)-2-allylamino]-3-phenyl-propionamide (0.50 g, 1.0 mmol), N-methylmorpholine-N-oxide (0.13 g, 1.1 mmol), acetone (15 mL), and water (20 mL). Add osmium tetraoxide (0.51 mL, 0.04M in THF, 0.021 mmol) and stir under an inert atmosphere for 18 hours. Pour the reaction mixture into a saturated solution of sodium bisulfite and extract the intermediate diol into ethyl acetate. Dry the separated organic layer over $MgSO_4$, filter, and evaporate in vacuo to give the crude diol which is used without further purification. Dissolve the crude diol in chloroform (10 mL). Add lead tetraacetate (0.48 g, 1.1 mmol) as a solution in chloroform (10 mL). Stir for 30 minutes. Pour the reaction into a saturated aqueous solution of sodium bicarbonate and extract with dichloromethane. Dry the separated organic layer over $MgSO_4$, filter and evaporate in vacuo to give the title compound. The title compound may be used without further purification.

EXAMPLE 62

(S)-N-Benzyl-N-methyl-2-[N'-(t-butoxycarbonyl)-
2-oxo-ethylamino]-3-(naphth-2-yl)-propionamide Scheme B, step g:

Combine (S)-N-benzyl-N-methyl-2-[N'-(t-butoxycarbonyl)-allylamino]-3-(naphth-2-yl)-propionamide (3.34 g, 7.29 mmol), and pyridine (0.03 ml) in dichloromethane/methanol (66 mL/7 mL). Cool to −78° C. Pass ozonized oxygen through the solution until a persistent light blue color is obtained. Pass nitrogen through the solution until the blue color dissipates. Add dimethyl sulfide (12 mL). Allow the reaction mixture to warm to ambient temperature and stir for 16 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting with 20% ethyl acetate/hexane to give the title compound: TLC R$_f$=0.70 (silica gel, 50% ethyl acetate/hexane).

EXAMPLE 63

(S)-N-(3,4-Dichlorobenzyl)-N-methyl-
2-[N'-(t-butoxycarbonyl)-2-oxo-ethylamino]-
3-(naphth-2-yl)-propionamide Scheme B, step g:

Combine (S)-N-(3,4-dichlorobenzyl)-N-methyl-2-[N'-(t-butoxycarbonyl)-allylamino]-3-(naphth-2-yl)-propionamide (0.26 g, 0.50 mmol), N-methylmorpholine-N-oxide (0.065 g, 0.55 mmol), acetone (10 mL), tetrahydrofuran (5 mL), and water (5 mL). Add osmium tetraoxide (0.26 mL, 0.04M in THF, 0.042 mmol) and stir under an inert atmosphere for 18 hours. Pour the reaction mixture into a saturated solution of sodium bisulfite and extract the intermediate diol into ethyl acetate. Dry the separated organic layer over MgSO$_4$, filter, and evaporate in vacuo to give the crude diol which is used without further purification. Dissolve the crude diol in chloroform (10 mL). Add a solution of lead tetraacetate (0.24 g, 0.55 mmol) in chloroform (10 mL). Stir for 30 minutes and then pour the reaction mixture into a saturated solution of sodium bicarbonate. Extract with dichloromethane and separate the organic layer. Dry the separated organic layer over MgSO$_4$, filter and evaporate in vacuo to give the title compound which may be used without further purification.

EXAMPLE 64

(S)-N-(2-Methoxybenzyl)-N-methyl-
2-[N'-(t-butoxycarbonyl)-2-oxo-ethylamino]-
3-(naphth-2-yl)-propionamide Scheme B, step g:

Combine (S)-N-(2-methoxybenzyl)-N-methyl-2-[N'-(t-butoxycarbonyl)-allylamino]-3-(naphth-2-yl)-propionamide (0.46 g, 0.96 mmol), N-methylmorpholine-N-oxide (0.12 g, 1.06 mmol), acetone (20 mL), and water (10 mL). Add osmium tetraoxide (0.50 mL, 0.04M in THF, 0.02 mmol) and stir under an inert atmosphere for 18 hours. Pour the reaction mixture into a saturated solution of sodium bisulfite and extract the intermediate diol into ethyl acetate. Dry the separated organic layer over MgSO$_4$, filter, and evaporate in vacuo to give the crude diol which is used without further purification. Dissolve the crude diol in chloroform (10 mL). Add a solution of lead tetraacetate (0.46 g, 1.06 mmol) in chloroform (10 mL). Stir for 30 minutes and then pour the reaction mixture into a saturated solution of sodium bicarbonate. Extract with dichloromethane and separate the organic layer. Dry the separated organic layer over MgSO$_4$, filter and evaporate in vacuo to give the title compound which may be used without further purification.

EXAMPLE 65

(S)-N-Benzyl-N-methyl-2-[N'-(t-butoxycarbonyl)-
3-hydroxypropylamino]-3-phenyl-propionamide Scheme B, optional step h:

Cool a solution of borane (1.5 mL, 1M in THF, 1.5 mmol) to 0° C. in an ice-bath under an inert atmosphere. Add cyclohexene (0.31 mL, 3.1 mmol) and stir for 15 minutes with continued cooling. Add the suspension of dicyclohexylborane in THF prepared above to (S)-N-Benzyl-N-methyl-2-[N'-(t-butoxycarbonyl)-allylamino]-3-phenyl-propionamide (2 mmol) and stir in an ice-bath for 15 minutes. Warm to ambient temperature and stir for 2 hours. Dilute the mixture with pH 7 phosphate buffer (40 mL) and ethanol (20 mL). Add 30% hydrogen peroxide (8 mL). Stir at ambient temperature for 20 hours. Concentrate in vacuo to obtain a residue. Dilute the reaction mixture with ethyl acetate and extract with water. Separate the layers, dry the organic layer over MgSO$_4$, filter, and evaporate in vacuo. Chromatograph on silica gel to give the title compound.

EXAMPLE 66

(S)-N-Benzyl-N-methyl-2-[N'-(t-butoxycarbonyl)-
3-oxo-propylamino]-3-phenyl-propionamide Scheme B, optional step i:

Combine (S)-N-Benzyl-N-methyl-2-[N'-(t-butoxycarbonyl)-3-hydroxypropylamino]-3-phenyl-propionamide (20 mmol), triethylamine (10 mmol), and dimethyl sulfoxide (4 mL). Add the solution prepared above to a solution of pyridine/sulfur trioxide complex (6.4 mmol) in dimethyl sulfoxide (12 mL). Stir for 1 hour. Dilute the reaction mixture with ethyl acetate and extract with water. Separate the layers, dry the organic layer over MgSO$_4$, filter, and evaporate in vacuo to give the title compound which is taken to the next step without further purification.

A general synthetic procedure is set forth in Scheme C for preparing the aldehyde of structure (3), in which G$_1$ is —C(O)— and G$_2$ is —CH$_2$—, used as a starting material in Scheme A. The reagents and starting materials are readily available to one of ordinary skill in the art. In Scheme E, all substituents, unless otherwise indicated, are as previously defined.

Scheme C

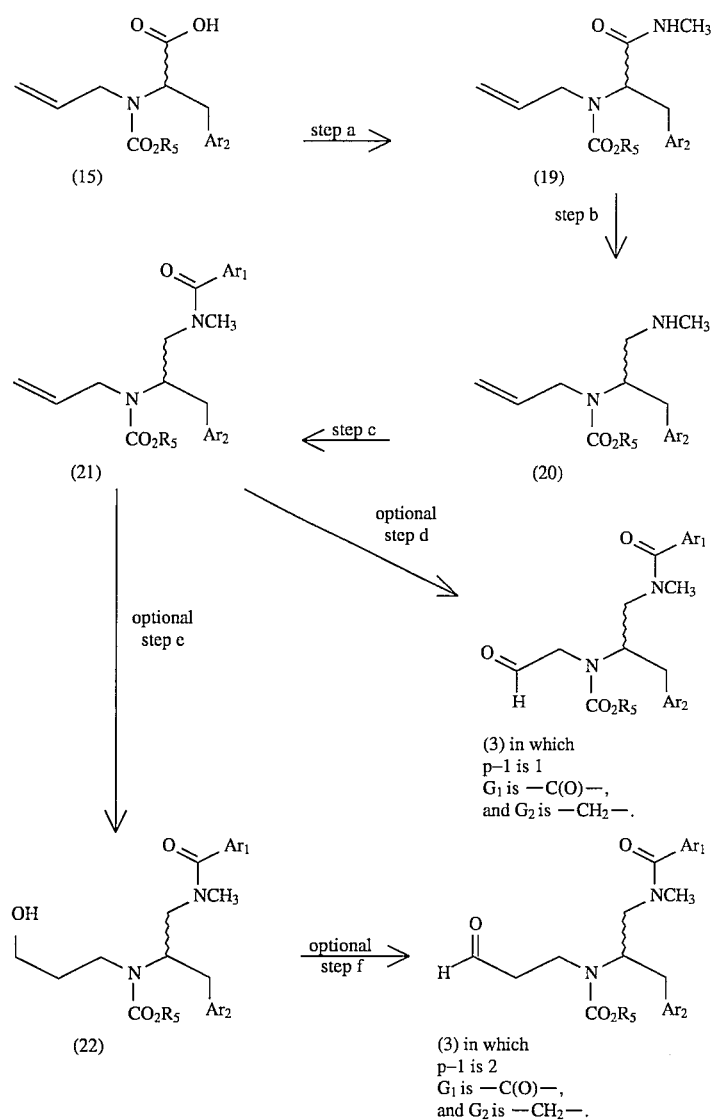

In Scheme C, step a, an appropriate allyl-carbamate acid of structure (15) prepared using the methods of Scheme B undergoes an amidation reaction with methylamine or a salt of methylamine to give an allyl-carbamate acid-N-methyl amide of structure (19).

An appropriate allyl-carbamate acid of structure (15) is one in which the stereochemistry, $R_5$, and $Ar_2$ are as desired in the product of formula (1). An appropriate allyl-carbamate acid of structure (15) can also be one in which the stereochemistry is as desired in the product of formula (1) and $Ar_2$ and $R_5$ give rise after deprotection to $Ar_2$ and $R_3$ as desired in the final product of formula (1). An appropriate allyl-carbamate acid of structure (15) can also be one in which the stereochemistry gives rise after resolution to stereochemistry as desired in the final product of formula (1) and $R_5$ and $Ar_2$ are as desired in the product of formula (1). An appropriate allyl-carbamate acid of structure (15) can also be one in which the stereochemistry gives rise after resolution to stereochemistry as desired in the final product of formula (1) and $Ar_2$ and $R_5$ give rise after deprotection to $Ar_2$ and $R_3$ as desired in the final product of formula (1).

An amidation reaction may proceed through an activated intermediate, such as a mixed anhydride or a (O)-hydroxybenzotriazole, which may be prepared but is not necessarily isolated before the addition of methylamine or salt of methylamine.

For example, an appropriate allyl-carbamate acid of structure (15) is contacted with 1.2 to 1.7 equivalents of a suitable base, such as N-methylmorpholine, in a suitable solvent, such as tetrahydrofuran. Generally, the reaction mixture is cooled to a temperature of between −50° C. and 0° C. with −25° C. to −20° C. being preferred, before the addition of 1.2 to 1.7 equivalents of isobutyl chloroformate. Generally, the reaction is allowed to stir for 30 minutes to 3 hours to allow for the formation of the mixed anhydride, an activated intermediate. While maintaining the temperature at between −50° C. and 0° C. methylamine or a salt of methyl amine is added. The reaction may, after the addition of amine is complete, be warmed to room temperature. The reaction requires from 2 to 48 hours. The product can be isolated and purified by techniques well known in the art, such as extraction, evaporation, chromatography, and recrystallization.

Alternatively, for example, an appropriate allyl-carbamate acid of structure (15) is contacted with a slight molar excess of methylamine or a salt of methylamine and 1-hydroxybenzotriazole hydrate in the presence of a slight molar excess of a coupling agent, such as dicyclohexylcarbodiimide or 1-(3-dimethylaminopropyl)-3-ethylcarbodiimide. The reaction is carried out in the presence of a suitable base, such as diisopropylethylamine. The reaction is carried out in a suitable solvent, such as dichloromethane or chloroform. The product can be isolated and purified by techniques well known in the art, such as extraction, evaporation, chromatography, and recrystallization.

In Scheme C, step b, an allyl-carbamate acid-N-methyl amide of structure (19) is reduced to give an N-methylamino compound of structure (20).

For example, an allyl-carbamate acid-N-methyl amide of structure (19) is contacted with a suitable reducing agent, such as diisobutylaluminum hydride or lithium aluminum hydride with diisobutylaluminum hydride being preferred. The reaction is carried out in a suitable solvent, such as tetrahydrofuran or toluene. Generally, the reaction is carried out at temperatures of from −20° C. to the refluxing temperature of the solvent. After an appropriate work-up, as is well known in the art, the work-up used depends on the products produced and the reducing reagent used, the product can be isolated and purified by techniques well known in the art, such as extraction, evaporation, chromatography, and recrystallization.

In Scheme C, step c, a N-methylamino compound of structure (20) is aroylated with an appropriate aroyl acid chloride to give a N-methyl aroylamide of structure (21).

An appropriate aroyl acid chloride, $Ar_1C(O)Cl$, is one in which $Ar_1$ is as desired in the product of formula (1) or give rise after deprotection to $Ar_1$ desired in the final product of formula (1).

For example, a N-methylamino compound of structure (20) is contacted with an appropriate aroyl acid chloride, $Ar_1C(O)Cl$. The reaction is carried out in the presence of a suitable base, such as triethylamine, diisopropylethylamine, or pyridine. The reaction is carried out in a suitable solvent, such as dichloromethane, chloroform, pyridine, dioxane, tetrahydrofuran, or water. Generally, the reaction is carried out at temperatures of form −20° C. to the refluxing temperature of the solvent. The product can be isolated and purified by techniques well known in the art, such as extraction, evaporation, chromatography, and recrystallization.

In Scheme C, optional step d, a N-methyl aroylamide of structure (21) is converted to an aldehyde of structure (3) in which $G_1$ is —C(O)—, $G_2$ is —$CH_2$—, and p-1 is 1. A N-methyl aroyl amide of structure (21) may be converted to an aldehyde of structure (3) in which $G_1$ is —C(O)—, $G_2$ is —$CH_2$—, and p-1 is 1 by either; ozonolysis in the presence of methanol followed by a reductive work-up, or an osmium tetraoxide mediated formation of an intermediate diol followed by oxidative cleavage with lead tetraacetate or sodium meta-periodate.

For example, a N-methyl aroylamide of structure (21) is contacted with ozone in the presence of methanol. The reaction is carried out in a suitable solvent, such as dichloromethane. Generally, the reaction is carried out a at temperature of from −100° C. to −60° C., with −70° C. being preferred. The reaction is worked-up reductively by the addition of a suitable reducing agent, such as tributylphosphine or dimethyl sulfide. The product may be isolated from the reaction zone by evaporation and may be used without further purification. The product may be purified by techniques well known in the art, such as chromatography and recrystallization.

Alternatively, for example, a N-methyl aroylamide of structure (21) is contacted with osmium tetraoxide to give an intermediate diol. The reaction may be carried out using a 0.01 to 0.05 molar equivalents of osmium tetraoxide and a slight molar excess of an oxidant, such as N-methylmorpholine-N-oxide. The reaction is carried out in a solvent, such as acetone/water mixtures. The reaction is carried out at ambient temperature and requires from 12 to 48 hours. The reaction mixture is added to a saturated solution of sodium bisulfite and the intermediate diol is isolated by extraction and evaporation and used without further purifications. The intermediate diol is contacted with a slight molar excess of lead tetraacetate or sodium meta-periodate. Generally, the reaction is carried out in a solvent, such as chloroform. The reaction is carried out at ambient temperature and requires from 30 minutes to 8 hours. The product may be isolated from the reaction zone by extraction and evaporation and may be used without further purification. The product may be purified by techniques well known in the art, such as chromatography and recrystallization.

In Scheme C, optional step e, a N-methyl aroylamide of structure (21) is contacted with an appropriate borane reagent followed oxidation with peroxide to give a N-methyl aroylamido alcohol of structure (22).

An appropriate borane reagent, such as dicyclohexylborane is one that reacts with a N-methyl aroylamide of structure (21) in a way that hydrogen peroxide oxidation gives a N-methyl aroylamido alcohol of structure (22).

For example, a N-methyl aroylamide of structure (21) is contacted with an appropriate borane reagent, such as dicyclohexylborane. The reaction is carried out in a suitable solvent, such as tetrahydrofuran. Generally, the reaction mixture is maintained at a temperature of from −20° C. to 10° C. during the combining of reactants. Generally, the reaction is carried out at ambient temperature. Generally, the borane formation reaction requires form 1 to 8 hours. A pH 7 phosphate buffer in a suitable solvent, such as ethanol is added before the addition of an excess of hydrogen peroxide. Generally, the oxidation requires from 8 to 48 hours and is carried out at ambient temperature. The product can be isolated and purified by techniques well known in the art, such as extraction, evaporation, chromatography, and recrystallization.

In Scheme C, optional step f, a N-methyl aroylamido alcohol of structure (22) is oxidized to give an aldehyde of structure (3) in which $G_1$ is —C(O)—, $G_2$ is —$CH_2$—, and p-1 is 2.

For example, two molar equivalents of dimethyl sulfoxide are added dropwise to a solution of oxalyl chloride, pyridine sulfur trioxide complex, or trifluoroacetic anhydride in dichloromethane, at approximately −60° C. After the addition is complete, the reaction is stirred for approximately two minutes. A molar equivalent of a N-methyl aroylamido alcohol of structure (22) as a solution in dichloromethane is added dropwise. After the addition is complete the reaction mixture is stirred for approximately forty minutes, then a 3-fold to 5-fold excess of triethylamine is added. The reaction mixture is allowed to stir with warming to ambient temperature over 1 hour to 5 hours. The product can be isolated and purified by techniques well known in the art, such as extraction, evaporation, chromatography, and recrystallization.

The following examples present typical syntheses as described in Scheme C. These examples are understood to be illustrative only and are not intended to limit the scope of the invention in any way.

EXAMPLE 67

(S)-N-Methyl-2-[N'-(t-butoxycarbonyl)-
allylamino]-3-phenyl-propionamide

Scheme C, step a:

Combine (S)-2-[N-(t-butoxycarbonyl)-allylamino]-3-phenyl-propionic acid (0.7 g, 2.29 mmol), 1-(3-dimethylaminopropyl)-3-ethylcarbodiimide hydrochloride (0.50 g, 2.52 mmol), 1-hydroxybenzotriazole (0.38 g, 2.52 mmol), methylamine hydrochloride (0.17 g, 2.52 mmol) and diisopropylethylamine (0.59 mL, 2.52 mmol) in dichloromethane (23 mL) and stir for 18 hours. Dilute with ethyl acetate and extract with 1M hydrochloric acid, a saturated aqueous solution ofسسsodium bicarbonate and a saturated aqueous solution of sodium chloride. Dry the separated organic layer over MgSO$_4$, filter and evaporate in vacuo. Chromatograph on silica gel eluting sequentially with 5% methanol/dichloromethane and 10% methanol/dichloromethane to give the title compound: TLC R$_f$=0.44 (silica gel, 30% ethyl acetate/hexane).

EXAMPLE 68

(S)-N-Methyl-2-[N'-(t-butoxycarbonyl)-allylamino]-
3-phenyl-propylamine

Scheme C, step b:

Dissolve (S)-N-methyl-2-[N'-(t-butoxycarbonyl)allylamino]-3-phenyl-propionamide (0.31 g, 0.98 mmol) in dichloromethane (10 mL) and cool in a dry ice/acetone bath to −78° C. Add diisobutylaluminum hydride (1.96 mL, 1.5M in toluene, 2.94 mmol). Allow to warm slowly to ambient temperature and stir for 16 hours. Slowly add a 15% aqueous solution of sodium hydroxide (3.0 mL). Extract with dichloromethane, dry the organic layer over MgSO$_4$, filter, and evaporate in vacuo to give the title compound as a mixture which is taken on to the next step without further purification.

EXAMPLE 69

(S)-N-Methyl-N-[[2-[N'-(t-butoxycarbonyl)-
allylamino]-3-phenylpropyl]-benzamide Scheme C, step c:

Combine (S)-N-methyl-2-[N'-(t-butoxycarbonyl)-allylamino]-3-phenyl-propylamine (1.23 g, 4.25 mmol) and diisopropylethylamine (0.36 mL, 2.0 mmol) in dichloromethane (20 mL). Cool to 0° C. in an ice bath. Add benzoyl chloride (0.24 mL, 2.0 mmol) and stir the reaction at 0° C. for 2 hours. Extract the reaction mixture with water, dry the organic layer over MgSO$_4$, filter, and evaporate in vacuo. Chromatograph on silica gel eluting with 20% ethyl acetate/hexane to give the title compound: TLC R$_f$=0.59 (silica gel, 20% ethyl acetate/hexane).

EXAMPLE 70

(S)-N-Methyl-N-[[2-[N'-(t-butoxycarbonyl)-
allylamino]-3-phenyl-propyl]-(3,4,5-trimethoxy)
benzamide Scheme C, step c:

Combine (S)-N-Methyl-2-[N'-(t-butoxycarbonyl)allylamino]-3-phenyl-propylamine (0.57 g, 1.87 mmol) and diisopropylethylamine (0.65 mL, 3.74 mmol) in dichloromethane (40 mL). Cool to 0° C. in an ice bath. Add 3,4,5-trimethoxybenzoyl chloride (0.43 g, 1.87 mmol) and stir the reaction at 0° C. for 4 hours. Extract the reaction mixture with water, dry the organic layer over MgSO$_4$, filter, and evaporate in vacuo. Chromatograph on silica gel eluting sequentially with 5% ethyl acetate/hexane, 20% ethyl acetate/hexane, 35% ethyl acetate/hexane to give the title compound.

EXAMPLE 71

(S)-N-Methyl-N-[[2-[N'-(t-butoxycarbonyl)-
2-oxo-ethylamino]-3-phenylpropyl]-
(3,4,5-trimethoxy)benzamide Scheme C, optional step d:

Combine (S)-N-methyl-N-[[2-[N'-(t-butoxycarbonyl)-allylamino]-3-phenylpropyl]-(3,4,5-trimethoxy)benzamide (0.145 g, 0.29 mmol), N-methylmorpholine-N-oxide (0.037 g, 0.32 mmol), acetone (5 mL), and water (5 mL). Add osmium tetraoxide (0.15 mL, 0.04M in THF, 0.006 mmol) and stir under an inert atmosphere for 18 hours. Pour the reaction mixture into a saturated solution of sodium bisulfite and extract the intermediate diol into ethyl acetate. Dry the separated organic layer over MgSO$_4$, filter, and evaporate in vacuo to obtain the crude diol which is used without further purification. Dissolve the crude diol in chloroform (10 mL). Add lead tetraacetate (0.32 g, 0.32 mmol) as a solution in chloroform (10 mL). Stir for 30 minutes. Pour the reaction into a saturated aqueous solution of sodium bicarbonate and extract with dichloromethane. Dry the separated organic layer over MgSO$_4$, filter and evaporate in vacuo to give the title compound: TLC R$_f$=0.79 (silica gel, 10% methanol/dichloromethane). The title compound may be used without further purification.

EXAMPLE 72

(S)-N-Methyl-N-[[2-[N'-(t-butoxycarbonyl)-
2-oxo-ethylamino]-3-phenylpropyl]-benzamide Scheme C, optional step d:

Combine (S)-N-methyl-N-[[2-[N'-(t-butoxycarbonyl)-allylamino]-3-phenylpropyl]-benzamide (0.14 g, 0.35 mmol), N-methylmorpholine-N-oxide (0.044 g, 0.38 mmol), acetone (5 mL), and water (5 mL). Add osmium tetraoxide (0.18 mL, 0.04M in THF, 0.0074 mmol) and stir under an inert atmosphere for 18 hours. Pour the reaction mixture into a saturated solution of sodium bisulfite and extract the intermediate diol into ethyl acetate. Dry the separated organic layer over MgSO$_4$, filter, and evaporate in vacuo to obtain the crude diol which is used without further purification. Dissolve the crude diol in chloroform (5 mL). Add lead tetraacetate (0.16 g, 0.38 mmol) as a solution in chloroform (5 mL). Stir for 30 minutes. Pour the reaction into a saturated aqueous solution of sodium bicarbonate and extract with dichloromethane. Dry the separated organic layer over MgSO$_4$, filter and evaporate in vacuo to give the title compound: TLC R$_f$=0.76 (silica gel, 50% ethyl acetate/hexane). The title compound may be used without further purification.

A general synthetic procedure is set forth in Scheme D for preparing the aldehyde of structure (3) in which G$_1$ is —C(O)— and G$_2$ is —C(O)— used as a starting material in Scheme A. The reagents and starting materials are readily available to one of ordinary skill in the art. In Scheme D, all substituents, unless otherwise indicated, are as previously defined.

Scheme D

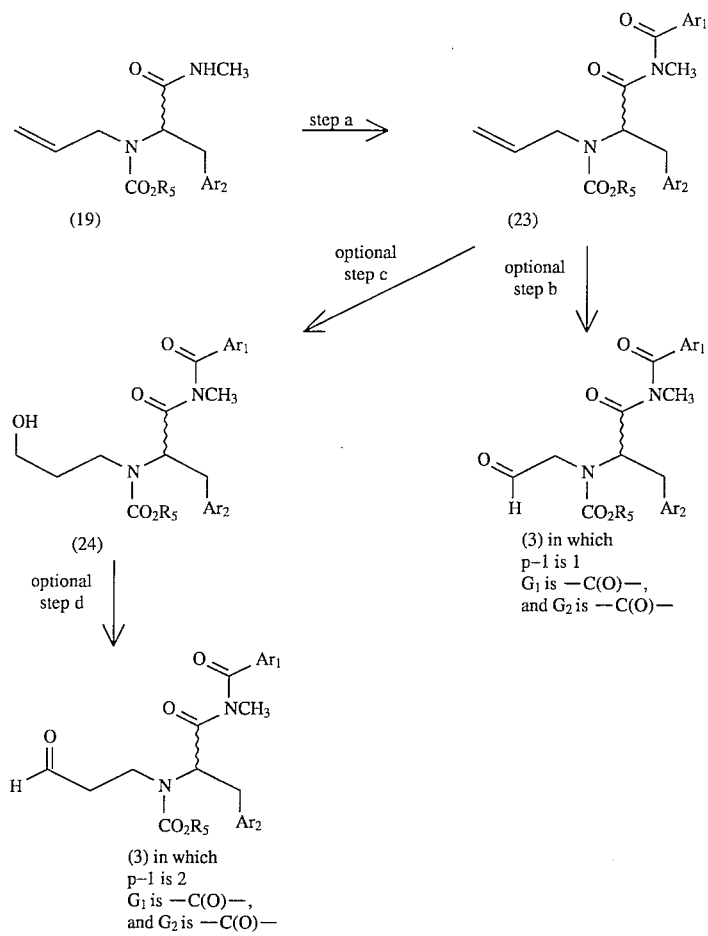

(3) in which
p-1 is 2
G₁ is —C(O)—,
and G₂ is —C(O)—

In Scheme D, step a, an appropriate allyl-carbamate acid-N-methyl amide of structure (19) prepared using the methods of Scheme C undergoes an imidation reaction with an appropriate acid chloride of structure Ar₁C(O)Cl to give a N-methyl imide of structure (23).

An appropriate allyl-carbamate acid-N-methyl amide of structure (19) is one in which the stereochemistry, R₅, and Ar₂ are as desired in the product of formula (1). An appropriate allyl-carbamate acid-N-methyl amide of structure (19) can also be one in which the stereochemistry is as desired in the product of formula (1) and Ar₂ and R₅ give rise after deprotection to Ar₂ and R₃ as desired in the final product of formula (1). An appropriate allyl-carbamate acid-N-methyl amide of structure (19) can also be one in which the stereochemistry gives rise after resolution to stereochemistry as desired in the final product of formula (1) and R₅ and Ar₂ are as desired in the product of formula (1). An appropriate allyl-carbamate acid-N-methyl amide of structure (19) can also be one in which the stereochemistry gives rise after resolution to stereochemistry as desired in the final product of formula (1) and Ar₂ and R₅ give rise after deprotection to Ar₂ and R₃ as desired in the final product of formula (1).

An appropriate acid chloride of structure Ar₁C(O)Cl is one in which Ar₁ is as desired in the product of formula (1) or can be one which gives rise after deprotection to Ar₁ desired in the final product of formula (1).

Imidation reactions are well known in the art and are described by Tull, R. et al, *J. Org. Chem.* 29, 2425 (1964) and Nagata, W. et al, *Annalen der Chemie*, 641, 184 (1964).

For example, an appropriate allyl-carbamate acid-N-methyl amide of structure (19) is contacted with an appropriate acid chloride of structure Ar₁C(O)Cl. The reaction is carried out in N,N-dimethylaniline. Generally, the reaction is carried out at temperatures of from 60° C. to 120° C. The product can be isolated and purified by techniques well known in the art, such as extraction, evaporation, chromatography, and recrystallization.

Alternately, for example, an appropriate allyl-carbamate acid-N-methyl amide of structure (19) is contacted, in a suitable solvent, such as toluene or tetrahydrofuran, with a suitable base, such as sodium hydride. The solution from above is contacted with an appropriate acid chloride of structure Ar₁C(O)Cl and then the reaction is generally heated to temperatures of from 50° C. to the refluxing temperature of the solvent. The product can be isolated and purified by techniques well known in the art, such as extraction, evaporation, chromatography, and recrystallization.

In Scheme D, optional step b, a N-methyl imide of structure (23) is converted to an aldehyde of structure (3) in which p-1 is 1, G₁ is —C(O)—, and G₂ is —C(O)—. The reaction carried out by the procedures generally taught in Scheme C optional step d.

In Scheme D, optional step c, a N-methyl imide of structure (23) is contacted with an appropriate borane reagent followed oxidation with peroxide to give an alcohol of structure (24). The reaction is carried out by the procedures generally taught in Scheme C, optional step e.

In Scheme D, optional step d, an alcohol of structure (24) is oxidized to give an aldehyde of structure (3) in which p-1 is 2, $G_1$ is —C(O)—, and $G_2$ is —C(O)—. The reaction is carried out by the procedures generally taught in Scheme C optional step f.

The following examples present typical syntheses as described in Scheme D. These examples are understood to be illustrative only and are not intended to limit the scope of the invention in any way.

EXAMPLE 73

(S)-N-Methyl-N-[[2-[N'-(t-butoxycarbonyl)-allylamino]-3-phenylpropyl]-benzimide

Scheme D, step a:

Combine (S)-N-methyl-2-[N'-(t-butoxycarbonyl)-allylamino]-3-phenyl-propionamide (5 mmol) and benzoyl chloride (5 mmol) in N,N-dimethylaniline (20 mL). Heat to 90° C. and stir for 24 hours. Evaporate in vacuo. Partition the reaction mixture between dichloromethane and water. Separate the organic layer, dry over $MgSO_4$, filter, and evaporate in vacuo. Chromatograph on silica gel to give the title compound.

EXAMPLE 74

(S)-N-Methyl-N-[[2-[N'-(t-butoxycarbonyl)-2-oxo-ethylamino]-3-phenylpropyl]-benzimide Scheme D, optional step b:

Combine (S)-N-methyl-N-[[2-[N'-(t-butoxycarbonyl)-allylamino]-3-phenylpropyl]-benzimide (1 mmol), N-methyl-morpholine-N-oxide (1.1 mmol), acetone (15 mL), and water (15 mL). Add osmium tetraoxide (0.48 mL, 0.04M in THF, 0.021 mmol) and stir under an inert atmosphere for 18 hours. Pour the reaction mixture into a saturated solution of sodium bisulfite and extract the intermediate diol into ethyl acetate. Dry the separated organic layer over $MgSO_4$, filter, and evaporate in vacuo. The crude diol is used without further purification. Dissolve the crude diol in chloroform (15 mL). Add lead tetraacetate (1.1 mmol) as a solution in chloroform (15 mL). Stir for 30 minutes. Pour the reaction into a saturated aqueous solution of sodium bicarbonate and extract with dichloromethane. Dry the separated organic layer over $MgSO_4$, filter and evaporate vacuo to give the title compound.

A general synthetic procedure is set forth in Scheme E for preparing the aldehyde of structure (3) in which $G_1$ is —$CH_2$—, and $G_2$ is —$CH_2$— used as a starting material in Scheme A. The reagents and starting materials are readily available to one of ordinary skill in the art. In Scheme E all substituents, unless otherwise indicated, are as previously defined.

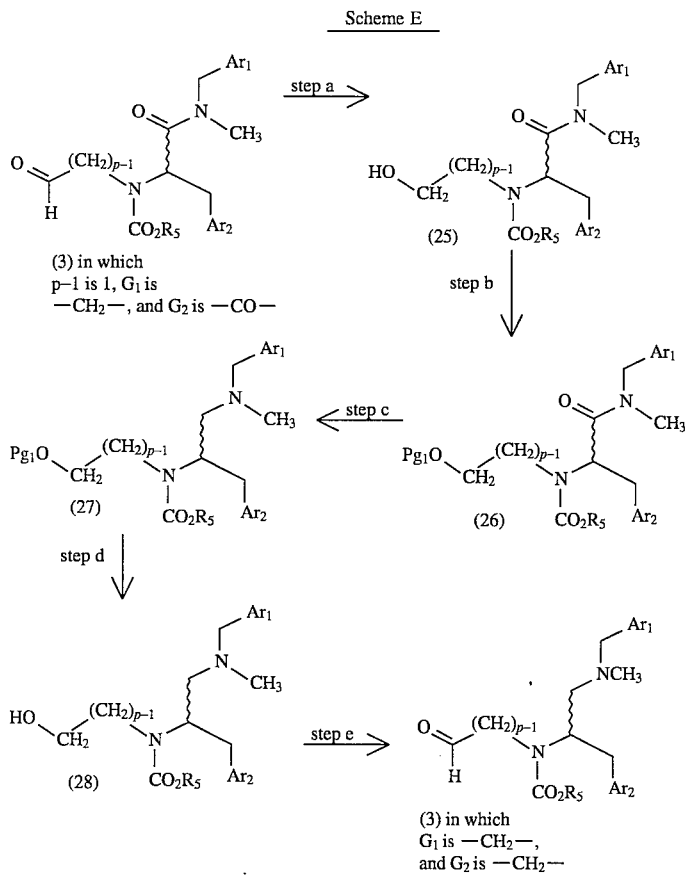

Scheme E

In Scheme E, step a, an appropriate aldehyde of structure (3) is reduced using a suitable reducing agent to give an alcohol amide of structure (25).

An appropriate aldehyde of structure (3) is one in which p-1 is 1 and $G_1$ is —$CH_2$—, $G_2$ is —C(O)—, the stereochemistry, $R_5$, $Ar_1$, $Ar_2$ are as is desired in the product of formula (1). An appropriate aldehyde of structure (3) can also be one in which p-1 is 1 and $G_1$ is —$CH_2$—, $G_2$ is —C(O)—, and the stereochemistry is as desired in the final product of formula (1) and $Ar_1$, $Ar_2$, and $R_5$ give rise after deprotection to $Ar_1$, $Ar_2$, and $R_3$ are as desired in the final product of formula (1). An appropriate aldehyde of structure (3) can also be one in which p-1 is 1 and $G_1$ is —$CH_2$—, $G_2$ is —C(O)—, $Ar_1$, $Ar_2$, and $R_3$ are as desired in the final product of formula (1) and the stereochemistry gives rise after resolution to stereochemistry as desired in the final product of formula (1). An appropriate aldehyde of structure (3) can also be one in which p-1 is 1 and $G_1$ is —$CH_2$—, $G_2$ is —C(O)—, are as desired in the final product of formula (1) and the stereochemistry gives rise after resolution to stereochemistry as desired in the final product of formula (1) and $Ar_1$, $Ar_2$, and $R_5$ give rise after deprotection to $Ar_1$, $Ar_2$, and $R_3$ are as desired in the final product of formula (1). For the preparation of aldehydes of structure (3) in which $G_1$ is —$CH_2$— and $G_2$ is —$CH_2$— from aldehydes (3) in which $G_1$ is —$CH_2$—, $G_2$ is —C(O)— the use of compounds in which $R_5$ is t-butyl is preferred.

For example, an appropriate aldehyde of structure (3) is contacted with from 1 to 4 equivalents of a suitable reducing agent, such as sodium borohydride. A suitable reducing agent is one which reduces an aldehyde and does not affect an amide of any protecting group which may be present. The reaction is carried out in a suitable solvent, such as methanol or ethanol. Generally, the reaction is carried out at temperatures of from 0° C. to the refluxing temperature of the solvent. Generally, the reactions require from 1 to 72 hours. The product can be isolated and purified by techniques well known in the art, such as quenching, extraction, evaporation, chromatography, and recrystallization.

In Scheme E, step b, an alcohol amide of structure (25) is protected using a suitable hydroxy protecting group, $Pg_1$, to give a protected hydroxy amide compound of structure (26). An alcohol amide of structure (25) in which p-1 is 2 is prepared as taught in Scheme B for an alcohol of structure (18). An alcohol amide of structure (25) in which p-1 is 2 is the same as an alcohol of structure (18) prepared in Scheme B.

A suitable hydroxy protecting group is one which allows for the reduction of an amide, such protecting groups include but are not limited to tetrahydropyran-2-yl, t-butyldimethylsilyl, or t-butyldiphenylsilyl. The selection and use of suitable hydroxy protecting groups is well known and appreciated in the art and is described in *Protecting Groups in Organic Synthesis* by T. Greene, Wiley-Interscience (1981).

In Scheme E, step c, a protected hydroxy amide compound of structure (26) is reduced using a suitable amide reducing agent to give a protected hydroxy amine compound of structure (27).

For example, a protected hydroxy amide compound of structure (26) is contacted with from 1 to 5 equivalents of a suitable amide reducing agent, such as lithium aluminum hydride, diisobutylaluminum hydride, or borane dimethyl sulfide complex. The reaction is carried out in a suitable solvent, such as tetrahydrofuran, toluene, or diethyl ether. Generally, the reaction is carried out at temperatures of from 0° C. to the refluxing temperature of the solvent. Generally, the reactions require from 1 to 72 hours. The product can be isolated and purified by techniques well known in the art, such as quenching, extraction, evaporation, chromatography, and recrystallization.

In Scheme E, step d, a protected hydroxy amine compound of structure (27) is deprotected to give a hydroxy amine compound of structure (28).

The use and removal of suitable hydroxy protecting groups is well known and appreciated in the art and is described in *Protecting Groups in Organic Synthesis* by T. Greene, Wiley-Interscience (1981).

As is appreciated by one of ordinary skill in the art, either an aldehyde of structure (3) in which $G_1$ is —$CH_2$— and $G_2$ is —C(O)— or an alcohol of structure (25) might be directly reduced to a hydroxy amine compound of structure (28) using a suitable amide reducing agent, such as lithium aluminum hydride, diisobutyl aluminum hydride, or borane dimethyl sulfide complex as taught in Scheme E, optional step d.

In Scheme E, step e, a hydroxy amine compound of structure (28) is oxidized to give an aldehyde of structure (3) in which $G_1$ is —$CH_2$—, $G_2$ is —$CH_2$—.

Oxidations of alcohols in compounds containing tertiary amines is well known and appreciated in the art and are described in T. P. Burkholder and P. L. Fuchs, *JACS* 112, 9601 (1990) and M. P. Kotick et al. *J. Med. Chem.* 26, 1050 (1983).

For example, two molar equivalents of dimethyl sulfoxide are added dropwise to a solution of trifluoroacetic anhydride in dichloromethane, at approximately −60° C. After the addition is complete, the reaction is stirred for approximately two minutes. A molar equivalent of a a hydroxy amine compound of structure (28) as a solution in dichloromethane is added dropwise. After the addition is complete the reaction mixture is stirred for approximately forty minutes, then a 3-fold to 5-fold excess of triethylamine is added. The reaction mixture is allowed to stir with warming to ambient temperature over 1 hour to 5 hours. The product can be isolated and purified by techniques well known in the art, such as extraction, evaporation, chromatography, and recrystallization.

The following examples present typical syntheses as described in Scheme E. These examples are understood to be illustrative only and are not intended to limit the scope of the invention in any way.

EXAMPLE 75

(S)-N-Benzyl-N-methyl-2-[N-(t-butoxycarbonyl)-2-hydroxy-ethylamino]-3-phenyl-propionamide Scheme E, step a:

Combine (S)-N-benzyl-N-methyl-2-[N-(t-butoxycarbonyl)-2-oxo-ethylamino]-3-phenyl-propionamide (5.0 mmol) and sodium borohydride (5.0 mmol) in ethanol (20 mL). Stir for 16 hours. Concentrate in vacuo to obtain a residue. Dilute the residue with ethyl acetate and extract with 0.5M hydrochloric acid solution and water. Separate the layers, dry the organic layer over $MgSO_4$, filter, and evaporate in vacuo to give the title compound.

EXAMPLE 76

(S)-N-Benzyl-N-methyl-2-[N-(t-butoxycarbonyl)-2-tetrahydropyran-2-yl-oxy-ethylamino]-3-phenyl-propionamide Scheme E, step b:

Combine (S)-N-benzyl-N-methyl-2-[N-(t-butoxycarbonyl)-2-hydroxy-ethylamino]-3-phenyl-propionamide (4 mmol) p-toluenesulfonic acid (50 mg), and dihydropyran (4 mmol)in anhydrous dichloromethane. After 8 hours, partition the reaction mixture between dichloromethane and 0.5M sodium hydroxide solution. Separate the organic layer and dry over $MgSO_4$, filter, and evaporate in vacuo to give the title compound.

EXAMPLE 77

(S)-N-Benzyl-N-methyl-2-[N-(t-butoxycarbonyl)-2-tetrahydropyran-2-yl-oxy-propylamino]-3-phenyl-propionamide Scheme E, step b:

Combine (S)-N-Benzyl-N-methyl-2-[N'-(t-butoxycarbonyl)-3-hydroxypropylamino]-3-phenyl-propionamide (4 mmol) p-toluenesulfonic acid (50 mg), and dihydropyran (4 mmol) in anhydrous dichloromethane. After 8 hours, partition the reaction mixture between dichloromethane and 0.5M sodium hydroxide solution. Separate the organic layer and dry over $MgSO_4$, filter, and evaporate in vacuo to give the title compound.

EXAMPLE 78

(S)-N-Benzyl-N-methyl-N-[N-(t-butoxycarbonyl)-2-tetrahydropyran-2-yl-oxy-ethylamino]-3-phenyl-propylamine Scheme E, step c:

Combine (S)-N-benzyl-N-methyl-2-[N-(t-butoxycarbonyl)-2-tetrahydropyran-2-yl-oxy-ethylamino]-3-phenyl-propionamide (4 mmol) and lithium aluminum hydride (8 mmol) in tetrahydrofuran (20 mmol ). Heat to reflux for 48 hours. Cool to ambient temperature, slowly add water (0.3 mL), 15% sodium hydroxide solution (0.3 mL), and water (0.9 mL). Stir until all the reagent is quenched. Filter and evaporate in vacuo to obtain a residue. Partition the residue between ethyl acetate and water. Separate the organic layer and dry over $MgSO_4$, filter, and evaporate in vacuo to give the title compound.

EXAMPLE 79

(S)-N-Benzyl-N-methyl-N-[N-(t-butoxycarbonyl)-2-tetrahydropyran-2-yl-oxy-propylamino]-3-phenyl-propylamine Scheme E, step c:

Combine (S)-N-benzyl-N-methyl-2-[N-(t-butoxycarbonyl)-2-tetrahydropyran-2-yl-oxy-propylamino]-3-phenyl-propionamide (4 mmol) and lithium aluminum hydride (8 mmol) in tetrahydrofuran (20 mmol). Heat to reflux for 48 hours. Cool to ambient temperature, slowly add water (0.3 mL), 15% sodium hydroxide solution (0.3 mL), and water (0.9 mL). Stir until all the reagent is quenched. Filter and evaporate in vacuo to obtain a residue. Partition the residue between ethyl acetate and water. Separate the organic layer and dry over $MgSO_4$, filter, and evaporate in vacuo to give the title compound.

EXAMPLE 80

(S)-N-Benzyl-N-methyl-N-[N-(t-butoxycarbonyl)-2-hydroxy-ethylamino]-3-phenyl-propylamine Scheme E, step d:

Combine (S)-N-benzyl-N-methyl-N-[N-(t-butoxycarbonyl)-2-tetrahydropyran-2-yl-oxy-ethylamino]-3-phenyl-propylamine (2.0 mmol) and p-toluenesulfonic acid (3 mmol) in methanol (20 mL). After 8 hours, evaporate in vacuo. Partition the residue between dichloromethane and 0.5M sodium hydroxide solution. Separate the organic layer and dry over $MgSO_4$, filter, and evaporate in vacuo to give the title compound.

EXAMPLE 81

(S)-N-Benzyl-N-methyl-N-[N-(t-butoxycarbonyl)-2-hydroxy-propylamino]-3-phenyl-propylamine Scheme E, step d:

Combine (S)-N-benzyl-N-methyl-N-[N-(t-butoxycarbonyl)-2-tetrahydropyran-2-yl-oxy-propylamino]-3-phenyl-propylamine (2.0 mmol) and p-toluenesulfonic acid (3 mmol) in methanol (20 mL). After 8 hours, evaporate in vacuo. Partition the residue between dichloromethane and 0.5M sodium hydroxide solution. Separate the organic layer and dry over $MgSO_4$, filter, and evaporate in vacuo to give the title compound.

EXAMPLE 82

(S)-N-Methyl-N-benzyl-N-[2-[N'-(t-butoxycarbonyl)-2-oxo-ethylamino]-3-phenyl-propylamine Scheme E, step e:

Combine trifluoroacetic acid anhydride (4.8 mmol) with dichloromethane (10 mL) and cool to –60° C. Add dropwise a solution of dimethyl sulfoxide (9.6 mmol) in dichloromethane (1 mL) while maintaining the temperature below –55° C. After addition is complete, stir for 2 minutes. Add a solution of (S)-N-benzyl-N-methyl-N-[N-(t-butoxycarbonyl)-2-hydroxy-ethylamino]-3-phenyl-propylamine (2 mmol) in dichloromethane and stir for 45 minutes. Cool the reaction to –78° C. and add triethylamine (10 mmol) dropwise. Allow the reaction to warm to ambient temperature and stir for 45 minutes. Pour the reaction into water. Extract this mixture with diethyl ether. Separate the organic layer and dry over $MgSO_4$, filter, and evaporate in vacuo to give the title compound.

EXAMPLE 83

(S)-N-Methyl-N-benzyl-N-[2-[N'-(t-butoxycarbonyl)-2-oxo-propylamino]-3-phenyl-propylamine Combine trifluoroacetic acid anhydride (4.8 mmol) with dichloromethane (10 mL) and cool to –60° C. Add dropwise a solution of dimethyl sulfoxide (9.6 mmol) in dichloromethane (1 mL) while maintaining the temperature below –55° C. After addition is complete, stir for 2 minutes. Add a solution of (S)-N-benzyl-N-methyl-N-[N-(t-butoxycarbonyl)-2-hydroxy-propylamino]-3-phenyl-propylamine (2 mmol) in dichloromethane and stir for 45 minutes. Cool the reaction to –78° C. and add triethylamine (10 mmol) dropwise. Allow the reaction to warm to ambient temperature and stir for 45 minutes. Pour the reaction into water. Extract this mixture with diethyl ether. Separate the organic layer and dry over $MgSO_4$, filter, and evaporate in vacuo to give the title compound.

The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptors types. The $NK_1$, $NK_2$, and $NK_3$ receptors are defined by the perferred binding affinity of substance P, neurokinin A (NKA), and neurokinin B (NKB), respectively.

Antagonism of the effects of substance P on its preferred receptor, i.e. $NK_1$, will not prevent the effects of NKA on its preferred receptor, i.e. $NK_2$. Therefore, the potential benefits of an antagonist with affinity at both the $NK_1$ and $NK_2$ receptors would be to reduce or prevent clinical manifestations of diseases and conditions which are mediated through both receptors.

The use of tachykinin antagonists is indicated as therapy for a variety of tachykinin-mediated diseases and conditions including: cystitis; bronchodilation; hypersensitivity reactions; the treatment of pain; peripheral neuropathy; post-herpetic neuralgia; adverse immunological reactions; respiratory diseases, such as asthma, bronchitis, cough, rhinitis, and allergies and the like; opthalmic diseases, such as conjuctivitis and vernal conjuctivitis; cutaneous diseases, such as contact dermatitis, atopic dermatitis, and urticaria; inflammatory diseases, such as rheumatoid arthritis and osteoarthritis, and the like; gastrointestinal conditions, such as Crohn's disease, emesis, and ulcerative colitis; conditions due to vasodilation, such as angina and migraine; and central nervous system diseases and conditions, such as anxiety, depression, psychosis, schizophrenia, dementia.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof. More particularly, the present invention provides compounds of formula (1) which are $NK_1$ receptor antagonists, $NK_2$ receptor antagonists, and both $NK_1$ and $NK_2$ receptor antagonists.

In a further embodiment, the present invention provides a method of treating tachykinin-mediated diseases and conditions in a patient in need thereof comprising administering to said patient a therapeutically effective amount of a compound of formula (1). Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular tachykinin-mediated disease or condition. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling tachykinin-mediated diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment of the tachykinin-mediated diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with tachykinin-mediated diseases and conditions described above, a compound of formula (1) can be administered in any form or mode which makes the compound bioavailable in an effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases and conditions, e.g. asthma. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 84

ANTAGONISM OF IODINATED TACHYKININ BINDING TO $NK_1$ AND $NK_2$ RECEPTORS BY PUTATIVE ANTAGONISTS

The $NK_1$ receptor affinity of proposed tachykinin antagonists was evaluated in guinea pig lungs (Keystone Biologicals, Cleveland, Ohio) and affinity for the $NK_2$ receptor evaluated in HSKR-1 cells (which are mouse 3T3 fibroblasts expressing the human jejunal $NK_2$ receptor). Tissues or cells were homogenized with a Polytron in 15 volumes of 50 mM Tris-HCl buffer (pH 7.4, 4° C.) and centrifuged. The pellet was resuspended in Tris-HCl buffer and was centrifuged; the pellet was washed twice by resuspension. The final pellet was resuspended at a concentration of 40 mg/ml for tissues and 20 mg/ml for cells in incubation buffer and remained at room temperature for at least 15 min prior to use. Receptor binding was initiated by addition of 250 ul membrane preparation in duplicate to 0.1 nM of the following radioligands: $^{125}$I-Bolton Hunter Lys-3 labeled substance P and $^{125}$iodohistidyl-1-neurokinin A; in a final volume of 500 ul of buffer containing 50 mM Tris-HCl (pH 7.4 at room temperature), 0.1% bovine serum albumin, 2 mM $MnCl_2$, 40 ug/ml bacitracin, 4 µg/ml leupeptin and chymostatin, 1 µM thiorphan and various doses of the putative tachykinin antagonists. Incubations were performed at room temperature for 90 min ($NK_1$ receptor assays) or 2 hr ($NK_2$ receptor assay); binding was terminated by addition of 50 mM Tris-HCl buffer (pH 7.4, 4° C.) and filtration under vacuum through GF/B filters presoaked with 0.1% polyethyleneimine (NK, receptor assays) or 0.5% bovine serum albumin ($NK_2$ receptor assay). Filter bound radioactivity was quantitated in a gamma counter. Nonspecific binding was defined as binding in the presence of 1 µM substance P or neurokinin A. Specific binding was calculated by subtracting nonspecific binding from total binding. Competition of iodinated SP or NKA binding by test compounds or standards was expressed as a percentage of this maximum competition. $IC_{50}$ values (concentration required to inhibit 50% of receptor binding) were generated for each of the test compounds by nonlinear regression using an iterative curve fitting program (GraphPAD Inplot, San Diego, Calif.).

$IC_{50}$ values for some of the compounds of the present invention are found in Table 1 and represent the mean of several experiments.

TABLE 1

BINDING AFFINITY ON THE $NK_1$ AND $NK_2$ RECEPTOR

| Compound No. | Receptor Binding Affinity | |
|---|---|---|
| | $NK_1$ $IC_{50}$ (M) | $NK_2$ $IC_{50}$ (M) |
| 1 | $2.57 \times 10^{-8}$ | $6.09 \times 10^{-7}$ |
| 2 | $6.15 \times 10^{-8}$ | $6.32 \times 10^{-7}$ |
| 3 | $9.29 \times 10^{-7}$ | $2.15 \times 10^{-7}$ |
| 4 | $1.46 \times 10^{-7}$ | $2.71 \times 10^{-7}$ |
| 5 | $7.81 \times 10^{-8}$ | $2.84 \times 10^{-7}$ |
| 6 | $2.94 \times 10^{-7}$ | $2.28 \times 10^{-7}$ |
| 7 | $4.72 \times 10^{-7}$ | $2.11 \times 10^{-7}$ |
| 8 | $7.11 \times 10^{-7}$ | $1.99 \times 10^{-6}$ |
| 9 | $7.78 \times 10^{-7}$ | $1.14 \times 10^{-7}$ |
| 10 | $6.31 \times 10^{-7}$ | $2.56 \times 10^{-6}$ |
| 11 | $9.53 \times 10^{-7}$ | $1.31 \times 10^{-7}$ |
| 12 | $1.43 \times 10^{-6}$ | $1.44 \times 10^{-6}$ |
| 13 | $2.41 \times 10^{-6}$ | $4.71 \times 10^{-6}$ |
| 14 | $1.0 \times 10^{-5}$ | $1.22 \times 10^{-6}$ |
| 15 | $>1.0 \times 10^{-5}$ | $2.56 \times 10^{-6}$ |
| 16 | $3.8 \times 10^{-6}$ | $1.58 \times 10^{-6}$ |

Compound No. 1 is (S)-N-(2-Methoxybenzyl)-N-methyl-2-[[(S)-2-(1H-indol-3-yl)-1-carboxymethyl-ethylamino]-ethylamino]-3-(naphth-2-yl)-propionamide;
Compound No. 2 is (S)-N-(3,4-Dichlorobenzyl)-N-methyl-2-[[(S)-2-(1H-indol-3-yl)-1-carboxymethyl-ethylamino]-ethylamino]-3-(naphth-2-yl)-propionamide;
Compound No. 3 is (S)-N-Benzyl-N-methyl-2-[[(R)-2-(1H-indol-3-yl)-1-carboxymethyl-ethylamino]-ethylamino]-3-phenyl-propionamide;
Compound No. 4 is (S)-N-(2-Methoxybenzyl)-N-methyl-2-[[(S)-2-(1H-indol-3-yl)-1-carboxymethyl-ethylamino]-ethylamino]-3-phenyl-propionamide;
Compound No. 5 is (S)-N-Benzyl-N-methyl-2-[[(S)-2-(1H-indol-3-yl)-1-carboxymethyl-ethylamino]-ethylamino]-3-(naphth-2-yl)-propionamide;
Compound No. 6 is (S)-N-Benzyl-N-methyl-2-[[(S)-2-(1H-indol-3-yl)-1-carboxymethyl-ethylamino]-ethylamino]-3-phenyl-propionamide;
Compound No. 7 is (S)-N-Benzyl-N-methyl-2-[[(S)-2-(1H-indol-3-yl)-1-carboxylic acid amide-ethylamino]-ethylamino]-3-phenyl-propionamide;
Compound No. 8 is (S)-N-(3,4,5-Trimethoxybenzyl)-N-methyl-2-[[(S)-2-(1H-indol-3-yl)-1-carboxymethyl-ethylamino]ethylamino]-3-phenyl-propionamide;
Compound No. 9 is (S)-N-Benzyl-N-methyl-2-[[2-(1H-indol-3-yl)-ethylamino]]-ethylamino]-3-phenyl-propionamide;
Compound No. 10 is N-Methyl-N-[(S)-2-[[(S)-2-(1H-indol-3-yl)-1-carboxymethyl-ethylamino]-ethylamino]-3-phenyl-propyl]-(3,4,5-trimethoxy-)benzamide;
Compound No. 11 is (S)-N-Benzyl-N-methyl-2-[[(R and S)-2-(1H-indol-3-yl)-1-methyl-ethylamino]-ethylamino]-3-phenyl-propionamide;
Compound No. 12 is (S)-N-Benzyl-N-methyl-2-[[(S)-2-phenyl-1-carboxymethyl-ethylamino]-ethylamino]-3-phenyl-propionamide;
Compound No. 13 is S)-N-Benzyl-N-methyl-2-[[(S)-1-phenyl-1-carboxymethyl-methylamino]-ethylamino]-3-phenyl-propionamide;
Compound No. 14 is N-Methyl-N-[(S)-2-[[(S)-2-(1H-indol-3-yl)-1-carboxymethyl-ethylamino]-ethylamino]-3-phenyl-propyl]-benzamide;
Compound No. 15 is (S)-N-Benzyl-N-methyl-2-[[(S)-2-(1H-indol-3-yl)-1-carboxymethyl-ethylamino]-N'-(t-butoxycarbonyl)ethylamino]-3-(naphth-2-yl)-propionamide;
Compound No. 16 is (S)-N-Benzyl-N-methyl-2-[[(S)-2-(1H-indol-3-yl)-1-carboxy-ethylamino]-ethylamino]-3-phenyl-propionamide.

EXAMPLE 85

ANTAGONISM OF TACHYKININ-INDUCED PHOSPHATIDYLINOSITOL (PI) TURNOVER IN VITRO BY PUTATIVE ANTAGONISTS

Tachykinin-mediated phosphatidylinositol (PI, inositol phosphate) accumulation was measured in UCII or SKLKB82#3 cells in the presence and absence of $NK_1$ or $NK_2$ receptor antagonists, respectively. Tissues were incubated in Krebs-Henseleit buffer at 37° C. with 95% $O_2$—5% $CO_2$ gassing. Tissues were then incubated with fresh buffer containing 100 µCi of myo-[2-$^3$H(N)] inositol at 37° C. for 60 min with gentle gassing. After washing twice in 5 ml room temperature buffer containing 10 mM LiCl, tissues were incubated for 30 min at room temperature with a buffer change at 15 min. Buffer was removed and Krebs-Henseleit buffer (containing 40 µg/ml bacitracin, 4 µg/ml each of leupeptin and chymostatin, 0.1% bovine serum albumin and 10 mM each of thiorphan and LiCl) including the test compound is added. After 15 min, SP was added to UCII cells or NKA to SKLKB82#3 cells at various concentrations to start the reaction. After incubation for 60 min at room temperature the reaction was terminated by addition of 930 µl chloroform: methanol (1:2 by volume) to each tube, followed by 310 µl chloroform and 310 µl doubly distilled water. Samples were vortexed, centrifuged, and 0.9 ml of the aqueous (top) phase removed and added to 2 ml doubly distilled $H_2O$. The mixture was vortexed and loaded onto a 50% Bio-Rad AG 1-X8 (formate form, 100–200 mesh) exchange column (Bio-Rad Laboratories, Hercules, Calif.). The columns were washed, in order, with: 1) 10 ml doubly distilled water, 2) 5 ml of 5 mM disodium tetraborate/60 mM sodium formate, and 3) 5 ml of 1M ammonium formate/ 0.1M formic acid. The third elution was collected and 1 ml counted in 7 ml scintillation fluid. A 50 µl aliquot of the organic (bottom) phase was removed, dried in a scintillation vial and counted in 7 ml scintillation fluid.

The ratio of DPM in the aqueous phase aliquot (total inositol phosphates) to the DPM in the 50 µl organic phase aliquot (total [$^3$H]inositol incorporated) was calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist). Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by SP. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. Data showing the in vitro effect of Compound No. 1, (S)-N-(2-Methoxybenzyl)-N-methyl-2-[[(S)-2-(1H-indol-3-yl)-1-carboxymethyl-ethylamino]-ethylamino]-3-(naphth-2-yl)-propionamide, is contained in Table 2. This compound produced no PI turnover when administered by itself suggesting a lack of agonist activity. The slope of the lines obtained by a Schild analysis are not significantly different from one (1) the compound is acting as a competitive antagonist. Data are the mean ±SEM (standard error of the mean). Values are derived from 3 experiments. Receptor source for $NK_1$ receptor is UCII cells and for $NK_2$ receptor is SKLKB82#3 cells.

TABLE 2

EFFECT OF COMPOUND 1 ON TACHYKININ-INDUCED PI TURNOVER IN VITRO

|  | in vitro activity | |
|---|---|---|
|  | $pA_2$ | −slope |
| $NK_1$ receptor | 7.34 | 1.28 |
| $NK_2$ receptor | 6.70 | 1.11 |

EXAMPLE 86

EVALUATION OF $NK_1$ AND $NK_2$ ANTAGONISM IN VIVO

One skilled in the art can determine that the compounds of the present intention are $NK_1$ receptor antagonists in vivo by evaluating the compounds ability to inhibit SP-induced plasma protein extravasation in guinea pig trachea. SP-induced protein leakage through postcapillary venules is assessed by measuring Evans Blue dye accumulation in guinea pig trachea. Animals are anesthetized with pentobarbital then injected with Evans Blue dye (20 mg/kg, i.v., prepared in 0.9% NaCl solution). One minute after dye administration, the antagonist is administered (i.v.) followed by SP (0.3 nmole/kg, i.v.) and, after 5 min, excess dye removed from the circulation by transcardiac perfusion with 50 ml 0.9% NaCl solution. The trachea and primary bronchi are removed, blotted dry and weighed. Dye quantitation is performed spectrophotometrically (620 nM) after extracting tissues in formamide for 24 hr at 50° C. Values are subtracted from background (dye only, no agonist). $ED_{50}$ (dose of compound which inhibits SP-induced plasma protein extravasation by 50%) is calculated from linear regression analysis.

One skilled in the art can determine that the compounds of the present intention are $NK_2$ receptor antagonists in vivo by evaluating the compounds ability to inhibit NKA-induced respiratory effects. In addition, both $NK_1$ and $NK_2$ antagonism can be evaluated after administration of capsaicin, which is known to release both SP and NKA from airway sensory nerves. Antagonism of NKA and capsaicin induced respiratory effects in conscious guinea pigs is carried out as follows. In vivo experiments are performed using male Duncan Hartley guinea pigs (250–350 g). Changes in conscious breathing patterns are monitored in four animals simultaneously using modified whole body plethysmography consisting of four small plexiglass boxes each connected to a reference box via Validyne DP 45-16 differential pressure transducers. The 4 boxes are equipped with an air supply line (also used for aerosol delivery) and an exhaust air line. Supply and exhaust lines are of the same length and narrow bore and arise from a common supply chamber and vented to a common exhaust chamber. This system is used to ensure that fluctuations in supply air and atmospheric pressure remain in phase and be eliminated from the net signal by the differential pressure transducers. The analog pressure signals are digitalized via a Data Translation DT2821 A to D board. Data are collected at a rate of 100 samples/second/animal. Each cycle of pressure change is analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles are characterized into normal breaths, forced exhalations (apparent by abdominal heaving), significant respiratory events (SREs; usually coughs, less often sneezes or gasps which are characterized by transient, extremely large pressure increases which are distinguishable from noise) and movement/noise with a PCAT 286 running a System V UNIX operating system. Dyspnea is defined as a significant, sustained increase in plethysmograph pressure which is associated with an observable shift to labored breathing in the animal.

During the course of a typical experiment in which airway responsiveness to various bronchoconstricting agents is examined, aerosols are delivered for 19 min (0.33 ml/min) using a DeVilbiss Ultraneb 99 ultrasonic nebulizer and animals monitored during this time. Prior to nebulization, 1 min of resting breathing is collected to establish a baseline pressure. In preliminary experiments, various concentrations of the bronchoconstrictive agents are evaluated and the concentration chosen which maximized the number of animals exhibiting dyspnea but minimized the severity of the response. Hence, neurokinin A is delivered at a final concentration of 0.05%, and capsaicin, 0.001% The vehicle for nebulization of all bronchoconstrictive agents is phosphate buffered saline (pH 7.4) which elicited no respiratory effects itself. Putative tachykinin antagonists are administered (i.v.) 20 min prior to onset of aerosol exposure.

What is claimed is:

1. A compound of the formula

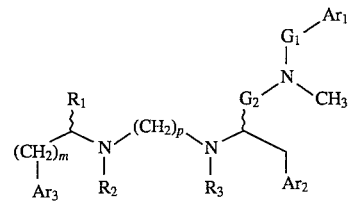

wherein $G_1$ is —$CH_2$— or —C(O)—;

$G_2$ is —$CH_2$— or —C(O)—;

p is 2 or 3;

m is 0 or 1;

$R_1$ is hydrogen, $C_1$–$C_4$ alkyl, —CHO, —C(O)$OR_4$, or —C(O)$NHR_4$, wherein $R_4$ is hydrogen, benzyl, or $C_1$–$C_4$ alkyl;

$R_2$ is hydrogen, or $C_1$–$C_4$ alkyl, $R_3$ is hydrogen or —C(O)$OR_5$ wherein $R_5$ is benzyl or $C_1$–$C_4$ alkyl;

$Ar_1$ is a radical chosen from the group:

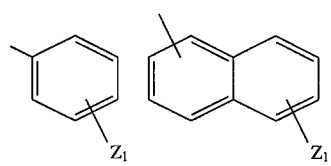

wherein $Z_1$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$Ar_2$ is a radical chosen from the group

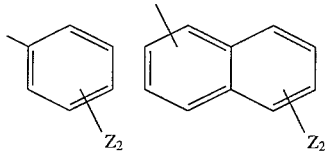

wherein $Z_2$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$Ar_3$ is a radical chosen from the group

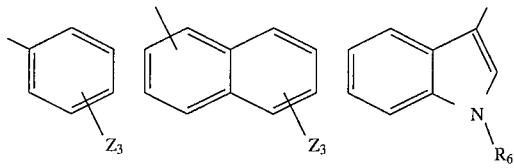

wherein $Z_3$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy; $R_6$ is hydrogen, $C_1$–$C_4$ alkyl, —CHO, —C(O)NHR$_7$, —(CH$_2$)$_n$NHC(NH)NH$_2$, —(CH$_2$)$_n$N(CH$_3$)$_2$, or —C(O)OR$_8$, wherein n is 2 or 3, $R_7$ is hydrogen, benzyl, or $C_1$–$C_4$ alkyl, and $R_8$ is benzyl or $C_1$–$C_4$ alkyl;

or stereoisomers, or a pharmaceutically acceptable salt thereof.

2. A compound of claim 1 wherein $R_3$ is hydrogen.

3. A compound of claim 2 wherein $R_2$ is hydrogen.

4. A compound of claim 3 wherein p is 2.

5. A compound of claim 4 wherein $G_1$ is —CH$_2$— and $G_2$ is —C(O)—.

6. A compound of claim 1 wherein the compound is (S)-N-Benzyl-N-methyl-2-[[(S)-2-[(1H-indol-3-yl)-1-carboxymethyl]-ethylamino]-N'-(t-butoxycarbonyl)-ethylamino]-3-phenyl-propionamide.

7. A compound of claim 1 wherein the compound is (S)-N-Benzyl-N-methyl-2-[[(R)-2-[(1H-indol-3-yl)-1-carboxymethyl]-ethylamino]-N'-(t-butoxycarbonyl)-ethylamino]-3-phenyl-propionamide.

8. A compound of claim 1 wherein the compound is (S)-N-Benzyl-N-methyl-2-[[(S)-2-phenyl-1-carboxymethyl]-ethylamino]-N'-(t-butoxycarbonyl)-ethylamino-3-phenyl-propionamide.

9. A compound of claim 1 wherein the compound is (S)-N-Benzyl-N-methyl-2-[[(S)-1-phenyl-1-carboxymethyl-methylamino]-N'-(t-butoxycarbonyl)-ethylamino]-3-phenyl-propionamide.

10. A compound of claim 1 wherein the compound is (S)-N-Benzyl-N-methyl-2-[[2-(1H-indol-3-yl)-ethylamino]-N'-(t-butoxycarbonyl)-ethylamino]-3-phenyl-propionamide.

11. A compound of claim 1 wherein the compound is (S)-N-Benzyl-N-methyl-2-[[(R and S)-2-(1H-indol-3-yl)-1-methyl-ethylamino]-N'-(t-butoxycarbonyl)-ethylamino]-3-phenyl-propionamide.

12. A compound of claim 1 wherein the compound is (S)-N-Benzyl-N-methyl-2-[[(S)-2-(1H-indol-3-yl)-1-carboxylic acid amide-ethylamino]-N'-(t-butoxycarbonyl)ethylamino]-3-phenyl-propionamide.

13. A compound of claim 1 wherein the compound is (S)-N-(2-Methoxybenzyl)-N-methyl-2-[[(S)-2-(1H-indol-3-yl)-1-carboxymethyl-ethylamino]-N'-(t-butoxycarbonyl)ethylamino]-3-phenyl-propionamide.

14. A compound of claim 1 wherein the compound is (S)-N-(3,4,5-Trimethoxybenzyl)-N-methyl-2-[[(S)-2-(1H-indol-3-yl)-1-carboxymethyl-N'-(t-butoxycarbonyl) ethylamino]ethylamino]-3-phenyl-propionamide.

15. A compound of claim 1 wherein the compound is (S)-N-Benzyl-N-methyl-2-[[(S)-2-(1H-indol-3-yl)-1-carboxymethyl-ethylamino]-N'-(t-butoxycarbonyl)ethylamino]-3-(naphth-2-yl)-propionamide.

16. A compound of claim 1 wherein the compound is (S)-N-(2-Methoxybenzyl)-N-methyl-2-[[(S)-2-(1H-indol-3-yl)-1-carboxymethyl-ethylamino]-N'-(t-butoxycarbonyl)ethylamino]-3-(naphth-2-yl)-propionamide.

17. A compound of claim 1 wherein the compound is (S)-N-(3,4-Dichlorobenzyl)-N-methyl-2-[[(S)-2-(1H-indol-3-yl)-1-carboxymethyl-ethylamino]-N'-(t-butoxycarbonyl) ethylamino]-3-(naphth-2-yl)-propionamide.

18. A compound of claim 1 wherein the compound is N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-(3,4,5-trimethoxy)benzamide.

19. A compound of claim 1 wherein the compound is N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-benzamide.

20. A compound of claim 1 wherein the compound is (S)-N-Benzyl-N-methyl-2-[[(S)-2-[(1H-indol-3-yl)-1-carboxymethyl]-ethylamino]-ethylamino]-3-phenyl-propionamide.

21. A compound of claim 1 wherein the compound is (S)-N-Benzyl-N-methyl-2-[[(R)-2-[(1H-indol-3-yl)-1-carboxymethyl]-ethylamino]-ethylamino]-3-phenyl-propionamide.

22. A compound of claim 1 wherein the compound is (S)-N-Benzyl-N-methyl-2-[[(S)-2-phenyl-1-carboxymethyl]-ethylamino]-ethylamino-3-phenyl-propionamide.

23. A compound of claim 1 wherein the compound is (S)-N-Benzyl-N-methyl-2-[[(S)-1-phenyl-1-carboxymethyl-methylamino]-N'-(t-butoxycarbonyl)-ethylamino]-3-phenyl-propionamide.

24. A compound of claim 1 wherein the compound is (S)-N-Benzyl-N-methyl-2-[[2-(1H-indol-3-yl)-ethylamino]-ethylamino]-3-phenyl-propionamide.

25. A compound of claim 1 wherein the compound is (S)-N-Benzyl-N-methyl-2-[[(R and S)-2-(1H-indol-3-yl)-1-methyl-ethylamino]-ethylamino]-3-phenyl-propionamide.

26. A compound of claim 1 wherein the compound is (S)-N-Benzyl-N-methyl-2-[[(S)-2-(1H-indol-3-yl)-1-carboxylic acid amide-ethylamino]-ethylamino]-3-phenyl-propionamide.

27. A compound of claim 1 wherein the compound is (S)-N-(2-Methoxybenzyl)-N-methyl-2-[[(S)-2-(1H-indol-3-yl)-1-carboxymethyl-ethylamino]-ethylamino]-3-phenyl-propionamide.

28. A compound of claim 1 wherein the compound is (S)-N-(3,4,5-Trimethoxybenzyl)-N-methyl-2-[[(S)-2-(1H-indol-3-yl)-1-carboxymethyl-ethylamino]ethylamino]-3-phenyl-propionamide.

29. A compound of claim 1 wherein the compound is (S)-N-Benzyl-N-methyl-2-[[(S)-2-(1H-indol-3-yl)-1-carboxymethyl-ethylamino]-ethylamino]-3-(naphth-2-yl)-propionamide.

30. A compound of claim 1 wherein the compound is (S)-N-(2-Methoxybenzyl)-N-methyl-2-[[(S)-2-(1H-indol-3-yl)-1-carboxymethyl-ethylamino]-ethylamino]-3-(naphth-2-yl)-propionamide.

31. A compound of claim 1 wherein the compound is (S)-N-(3,4-Dichlorobenzyl)-N-methyl-2-[[(S)-2-(1H-indol-3-yl)-1-carboxymethyl-ethylamino]-N'-(t-butoxycarbonyl) ethylamino]-3-(naphth-2-yl)-propionamide.

32. A compound of claim 1 wherein the compound is N-Methyl-N-[(S)-2-[[(S)-2-(1H-indol-3-yl)-1-carboxymethyl-ethylamino]-N'-(t-butoxycarbonyl)-ethylamino]-3-phenyl-propyl]-(3,4,5-trimethoxy)benzamide.

33. A compound of claim 1 wherein the compound is N-Methyl-N-[(S)-2-[[(S)-2-(1H-indol-3-yl)-1-carboxymethyl-ethylamino]-ethylamino]-3-phenyl-propyl]-benzamide.

34. A pharmaceutical composition comprising a compound of claim 1 and a pharmaceutically acceptable carrier.

35. A pharmaceutical composition comprising a compound of claims 2–5 and a pharmaceutically acceptable carrier.

36. A pharmaceutical composition comprising a compound of claims 6–33 and a pharmaceutically acceptable carrier.

37. A method for treating tachykinin-mediated diseases and conditions in a patient in need thereof comprising administering to said patient a therapeutically effective amount of a compound of claim 1.

38. A method for treating asthma in a patient in need thereof comprising administering to said patient a therapeutically effective amount of a compound of claim 1.

39. A method for treating cough in a patient in need thereof comprising administering to said patient a therapeutically effective amount of a compound of claim 1.

40. A method for treating bronchitis in a patient in need thereof comprising administering to said patient a therapeutically effective amount of a compound of claim 1.

* * * * *

UNITED STATES PATENT AND TRADEMARK OFFICE
CERTIFICATE OF CORRECTION

PATENT NO. : 5,597,845

DATED : January 28, 1997

INVENTOR(s) : Timothy P. Burkholder, et al.

It is certified that error appears in the above-identified patent and that said Letters Patent is hereby corrected as shown below:

At column 10, line 50, the patent reads "[[4(S)" and should read --[[(S)--.
At column 15, line 41, the patent reads "ethylamino 3-3-phenyl" and should read --ethylamino]-3-phenyl--.
At column 15, line 67, the patent reads "C31H36N4" and should read -- $C_{31}H_{36}N_4$ --.
At column 21, line 38, the patent reads "-37-yl" and should read -- -3-yl)- --.

Signed and Sealed this

First Day of September, 1998

Attest:

BRUCE LEHMAN

*Attesting Officer*

*Commissioner of Patents and Trademarks*